United States Patent [19]

Doria et al.

[11] Patent Number: 4,521,419
[45] Date of Patent: Jun. 4, 1985

[54] CONDENSED CYCLOALIPHATIC DERIVATIVES OF SUBSTITUTED PYRIDO[1,2-A]PYRIMIDINES AND METHODS OF TREATING ALLERGIC CONDITIONS, PEPTIC ULCERS AND INHIBITING GASTRIC ACID SECRETION WITH THEM

[75] Inventors: Gianfederico Doria, Milan; Carlo Passarotti, Gallarate; Pier P. Lovisolo; Ada Buttinoni, both of Milan, all of Italy

[73] Assignee: Farmitalia Carlo Erba S.p.A., Milan, Italy

[21] Appl. No.: 489,057

[22] Filed: Apr. 27, 1983

[30] Foreign Application Priority Data

Apr. 29, 1982 [GB] United Kingdom ............... 8212429
Apr. 6, 1983 [GB] United Kingdom ............... 8309259

[51] Int. Cl.$^3$ ............... A61K 31/505; C07D 471/04
[52] U.S. Cl. ............... 514/267; 544/248; 544/252
[58] Field of Search ............... 544/252, 248; 542/429; 424/251

[56] References Cited

U.S. PATENT DOCUMENTS

| 3,935,197 | 1/1976 | Yale | 424/251 X |
| 3,965,100 | 6/1976 | Yale | 424/251 |
| 4,033,961 | 7/1977 | Scwender et al. | 424/251 X |
| 4,066,767 | 1/1978 | Schwender et al. | 424/251 |
| 4,083,980 | 4/1978 | Schromm et al. | 424/251 |
| 4,123,533 | 10/1978 | Hermecz et al. | 424/251 |
| 4,310,526 | 1/1982 | Doria et al. | 424/251 X |
| 4,428,952 | 1/1984 | Doria et al. | 424/251 |

OTHER PUBLICATIONS

Shakhidoyatov, et al., Chemical Abstracts, vol. 88, 7166j (1978).

Primary Examiner—Diana G. Rivers
Attorney, Agent, or Firm—Murray, Whisenhunt and Ferguson

[57] ABSTRACT

Compounds of the formula (1)

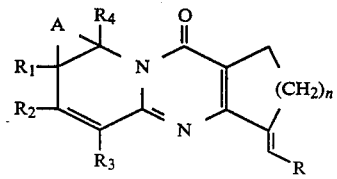

wherein
n is 1 or 2;
$R_1$ represents a hydrogen or a halogen atom, a $C_1$–$C_4$ alkyl group, a —CN group, a —$CONH_2$ group or a —$COOR_8$ group, wherein $R_8$ represents hydrogen or a $C_1$–$C_6$ alkyl group, unsubstituted or substituted by di($C_1$–$C_4$) - alkylamino;

each of $R_2$, $R_3$ and $R_4$ independently represents a hydrogen or a halogen atom, a $C_1$–$C_4$ alkyl group, a $C_1$–$C_4$ alkoxy group or a $C_3$–$C_4$ alkenyloxy group;

A completes a bond, thereby providing a double bond or, when $R_1$ is —$COOR_8$ wherein $R_8$ is as defined above, A may represent also a —$CH_2$— group, thereby providing a cyclopropane ring fused to the pyrido ring;

R is (a) furyl, thienyl or pyridyl; or
(b) a group of formula

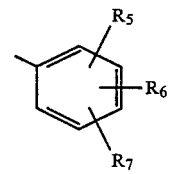

wherein
each of $R_5$, $R_6$ and $R_7$ represents, independently, a hydrogen or a halogen atom, hydroxy, formyloxy, $C_2$–$C_8$ alkanoyloxy, $C_1$–$C_4$ alkyl, $C_1$–$C_4$ alkoxy, nitro or a

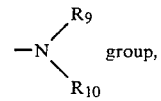

wherein each of $R_9$ and $R_{10}$ independently represents hydrogen, $C_1$–$C_4$ alkyl, formyl or $C_2$–$C_8$ alkanoyl, or adjacent groups represented by two of $R_5$, $R_6$ and $R_7$, taken together, form a $C_1$–$C_3$ alkylenedioxy group; and the pharmaceutically acceptable salts thereof have pharmaceutical activity in the treatment of allergic conditions and peptic ulcers, and inhibit the secretion of gastric acid.

10 Claims, No Drawings

CONDENSED CYCLOALIPHATIC DERIVATIVES OF SUBSTITUTED PYRIDO[1,2-A]PYRIMIDINES AND METHODS OF TREATING ALLERGIC CONDITIONS, PEPTIC ULCERS AND INHIBITING GASTRIC ACID SECRETION WITH THEM

DESCRIPTION

The present invention relates to new condensed cycloaliphatic derivatives of substituted pyrido[1,2-a]pyrimidines, to a process for their preparation and to pharmaceutical compositions containing them.

The invention provides compounds having the following general formula (I)

(I)

wherein n is 1 or 2;

$R_1$ represents a hydrogen or a halogen atom, a $C_1$–$C_4$ alkyl group, a —CN group, a —$CONH_2$ group or a —$COOR_8$ group, wherein $R_8$ represents hydrogen or a $C_1$–$C_6$ alkyl group, unsubstituted or substituted by di($C_1$–$C_4$)-alkylamino;

each of $R_2$, $R_3$ and $R_4$ independently represents a hydrogen or a halogen atom, a $C_1$–$C_4$ alkyl group, a $C_1$–$C_4$ alkoxy group or a $C_3$–$C_4$ alkenyloxy group;

A completes a bond, thereby providing a double bond or, when $R_1$ is —$COOR_8$ wherein $R_8$ is as defined above, A may represent also a —$CH_2$— group, thereby providing a cyclopropane ring fused to the pyrido ring;

R is (a) furyl, thienyl or pyridyl; or (b) a group of formula wherein each of $R_5$, $R_6$ and $R_7$ represents, independently, a hydrogen or a halogen atom, hydroxy, formyloxy, $C_2$–$C_8$ alkanoyloxy, $C_1$–$C_4$ alkyl, $C_1$–$C_4$ alkoxy, nitro or a —N(R_9)(R_{10}) group, wherein each of $R_9$ and $R_{10}$ independently represents hydrogen, $C_1$–$C_4$ alkyl, formyl or $C_2$–$C_8$ alkanoyl, or adjacent groups represented by two of $R_5$, $R_6$ and $R_7$, taken together, form a $C_1$–$C_3$ alkylenedioxy group; and the pharmaceutically acceptable salts thereof.

The invention also includes within its scope all the possible isomers, e.g. stereoisomers and optical isomers and their mixtures, and the metabolites and the metabolic precursors of the compounds of formula (I).

The numbering used to identify the position in the compounds of formula (I) is the conventional one, as is depicted in the following examples:

(A) when n=1:

(B) when n=2:

From the above definition of the meanings of the symbol A, it is clear that, whichever are the meanings of $R_1$, A can always complete a bond, thereby providing a double bond between the 7- and 8-carbon atoms in the compounds wherein n is one or between the 8- and 9-carbon atoms in the compounds wherein n is two, while, when $R_1$ is —$COOR_8$, A can not only complete a bond but also represent a —$CH_2$— group. The alkyl, alkoxy, alkanoyl and alkanoyloxy groups may be branched or straight chain groups.

When one or more of $R_1$, $R_2$, $R_3$ and $R_4$ is $C_1$–$C_4$ alkyl, this is preferably a methyl group.

When $R_8$ is an unsubstituted $C_1$–$C_6$ alkyl group, it is preferably methyl, ethyl, isopropyl, hexyl, n-butyl.

When one or more of $R_1$, $R_2$, $R_3$, $R_4$ is a halogen atom, it is preferably chlorine or bromine.

When one or more of $R_5$, $R_6$ and $R_7$ is halogen, it is preferably fluorine or chlorine.

When one or more of $R_5$, $R_6$ and $R_7$ is $C_1$–$C_4$ alkyl, it is preferably methyl or ethyl.

When one or more of $R_5$, $R_6$ and $R_7$ is $C_1$–$C_4$ alkoxy, it is preferably methoxy, ethoxy, propoxy and isopropoxy.

When one or both of $R_9$ and $R_{10}$ is $C_1$–$C_4$ alkyl, it is preferably methyl or ethyl.

Preferred alkanoyloxy groups are acetoxy and propionyloxy.

Preferred alkanoyl groups are acetyl and propionyl.

Preferred compounds of the invention are compounds having formula (I) wherein $R_1$ represents hydrogen, chlorine, carboxy, methyl, or ($C_1$–$C_4$)alkoxycarbonyl unsubstituted or substituted by a 2-N,N-di($C_1$–$C_2$)alkyl-amino group; $R_2$ is hydrogen; $R_3$ is hydrogen, chlorine, methyl or methoxy; $R_4$ is hydrogen; A completes a bond, thereby providing a double bond, or when $R_1$ is a free carboxy group, A may represent also a —$CH_2$— group, thereby providing a cyclopropane ring fused to the pyrido ring; n is 1 or 2; R is (a) furyl, thienyl or pyridyl; or (b) a group of formula

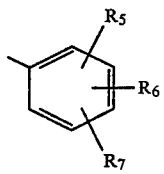

wherein, each of $R_5$, $R_6$ and $R_7$ represents independently hydrogen, chlorine, fluorine, $C_1$–$C_2$ alkyl, $C_1$–$C_3$ alkoxy, amino, dimethylamino, hydroxy or adjacent groups represented by two of $R_5$, $R_6$ and $R_7$, taken together, form a methylenedioxy group; and the pharmaceutically acceptable salts thereof.

Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine, di-(2-ethylhexyl)-amine, piperidine, N-ethylpiperidine, N,N-diethylaminoethylamine, N-ethylmorpholine, 2-phenethylamine, N-benzyl-β-phenethylamine, N-benzyl-N,N-dimethylamine and the other acceptable organic amines, as well as the salts with inorganic acids, e.g. hydrochloric, hydrobromic, nitric and sulphuric acids and with organic acids, e.g. citric, tartaric, maleic, malic, fumaric, methanesulphonic and ethanesulphonic acids.

Preferred salts are the sodium and the potassium salts, as well as the hydrochlorides of the basic esters, e.g. the diethylaminoethyl and dimethylaminoethyl esters.

Examples of particularly preferred compounds of the invention are:

3-benzylidene-1,2,3,10-tetrahydro-10-oxo-cyclopenta[d]pyrido[1,2-a]pyrimidine-7-carboxylic acid;

3-(2-methyl-benzylidene)-1,2,3,10-tetrahydro-10-oxo-cyclopenta[d]pyrido[1,2-a]pyrimidine-7-carboxylic acid;

3-(2,5-dimethoxy-benzylidene)-1,2,3,10-tetrahydro-10-oxo-cyclopenta[d]pyrido[1,2-a]pyrimidine-7-carboxylic acid;

3-(2,3-dimethoxy-benzylidene)-1,2,3,10-tetrahydro-10-oxo-cyclopenta[d]pyrido[1,2-a]pyrimidine-7-carboxylic acid;

3-(2-methoxy-3-ethoxy-benzylidene)-1,2,3,10-tetrahydro-10-oxo-cyclopenta[d]pyrido[1,2-a]pyrimidine-7-carboxylic acid;

3-(3-methyl-benzylidene)-1,2,3,10-tetrahydro-10-oxo-cyclopenta[d]pyrido[1,2-a]pyrimidine-7-carboxylic acid;

3-(4-methyl-benzylidene)-1,2,3,10-tetrahydro-10-oxo-cyclopenta[d]pyrido[1,2-a]pyrimidine-7-carboxylic acid;

3-(2-ethoxy-benzylidene)-1,2,3,10-tetrahydro-10-oxo-cyclopenta[d]pyrido[1,2-a]pyrimidine-7-carboxylic acid;

3-(3-ethoxy-benzylidene)-1,2,3,10-tetrahydro-10-oxo-cyclopenta[d]pyrido[1,2-a]pyrimidine-7-carboxylic acid;

3-(4-methoxy-benzylidene)-1,2,3,10-tetrahydro-10-oxo-cyclopenta[d]pyrido[1,2-a]pyrimidine-7-carboxylic acid;

3-(4-ethoxy-benzylidene)-1,2,3,10-tetrahydro-10-oxo-cyclopenta[d]pyrido[1,2-a]pyrimidine-7-carboxylic acid;

3-(2-methoxy-benzylidene)-1,2,3,10-tetrahydro-10-oxo-cyclopenta[d]pyrido[1,2-a]pyrimidine-7-carboxylic acid;

3-(3-methoxy-benzylidene)-1,2,3,10-tetrahydro-10-oxo-cyclopenta[d]pyrido[1,2-a]pyrimidine-7-carboxylic acid;

3-benzylidene-7,8-methylene-1,2,3,10-tetrahydro-10-oxo-cyclopenta[d]pyrido[1,2-a]pyrimidine-7-carboxylic acid;

3-(2-methyl-benzylidene)-7,8-methylene-1,2,3,10-tetrahydro-10-oxo-cyclopenta[d]pyrido[1,2-a]pyrimidine-7-carboxylic acid;

4-benzylidene-1,2,3,4-tetrahydro-11-oxo-11H-pyrido[2,1-b]quinazoline-8-carboxylic acid;

4-(2-methyl-benzylidene)-1,2,3,4-tetrahydro-11-oxo-11H-pyrido[2,1-b]quinazoline-8-carboxylic acid;

4-(3-methyl-benzylidene)-1,2,3,4-tetrahydro-11-oxo-11H-pyrido[2,1-b]quinazoline-8-carboxylic acid;

4-(4-methyl-benzylidene)-1,2,3,4-tetrahydro-11-oxo-11H-pyrido[2,1-b]quinazoline-8-carboxylic acid;

4-(2-methoxy-benzylidene)-1,2,3,4-tetrahydro-11-oxo-11H-pyrido[2,1-b]quinazoline-8-carboxylic acid;

4-(3-methoxy-benzylidene)-1,2,3,4-tetrahydro-11-oxo-11H-pyrido[2,1-b]quinazoline-8-carboxylic acid;

4-(4-methoxy-benzylidene)-1,2,3,4-tetrahydro-11-oxo-11H-pyrido[2,1,b]quinazoline-8-carboxylic acid;

4-(2-ethoxy-benzylidene)-1,2,3,4-tetrahydro-11-oxo-11H-pyrido[2,1-b]quinazoline-8-carboxylic acid;

4-(3-ethoxy-benzylidene)-1,2,3,4-tetrahydro-11-oxo-11H-pyrido[2,1-b]quinazoline-8-carboxylic acid;

4-(4-ethoxy-benzylidene)-1,2,3,4-tetrahydro-11-oxo-11H-pyrido[2,1-b]quinazoline-8-carboxylic acid;

4-(2,5-dimethyl-benzylidene)-1,2,3,4-tetrahydro-11-oxo-11H-pyrido[2,1-b]quinazoline-8-carboxylic acid;

4-(2,3-dimethoxy-benzylidene)-1,2,3,4-tetrahydro-11-oxo-11H-pyrido[2,1-b]quinazoline-8-carboxylic acid;

4-(2,5-dimethoxy-benzylidene)-1,2,3,4-tetrahydro-11-oxo-11H-pyrido[2,1-b]quinzoline-8-carboxylic acid;

4-(2,6-dichloro-benzylidene)-1,2,3,4-tetrahydro-11-oxo-11H-pyrido[2,1-b]quinazoline-8-carboxylic acid;

4-(3,4-dichloro-benzylidene)-1,2,3,4-tetrahydro-11-oxo-11H-pyrido[2,1-b]quinazoline-8-carboxylic acid;

4-(3,4-dimethoxy-benzylidene)-1,2,3,4-tetrahydro-11-oxo-11H-pyrido[2,1-b]quinazoline-8-carboxylic acid;

4-(3,4-methylenedioxy-benzylidene)-1,2,3,4-tetrahydro-11-oxo-11H-pyrido[2,1-b]quinazoline-8-carboxylic acid;

4-(4-fluoro-benzylidene)-1,2,3,4-tetrahydro-11-oxo-11H-pyrido[2,1-b]quinazoline-8-carboxylic acid;

4-(2-chloro-benzylidene)-1,2,3,4-tetrahydro-11-oxo-11H-pyrido[2,1-b]quinazoline-8-carboxylic acid;

4-(3-chloro-benzylidene)-1,2,3,4-tetrahydro-11-oxo-11H-pyrido[2,1-b]quinazoline-8-carboxylic acid;

4-(4-chloro-benzylidene)-1,2,3,4-tetrahydro-11-oxo-11H-pyrido[2,1-b]quinazoline-8-carboxylic acid;

4-(2-methoxy-3-ethoxy-benzylidene)-1,2,3,4-tetrahydro-11-oxo-11H-pyrido[2,1-b]quinazoline-8-carboxylic acid;

4-(2-thienylidene)-1,2,3,4-tetrahydro-11-oxo-11H-pyrido[2,1-b]quinazoline-8-carboxylic acid;

4-[(2-pyridyl)-methylene]-1,2,3,4-tetrahydro-11-oxo-11H-pyrido[2,1-b]quinazoline-8-carboxylic acid;

4-[(3-pyridyl)-methylene]-1,2,3,4-tetrahydro-11-oxo-11H-pyrido[2,1-b]quinazoline-8-carboxylic acid;

4-benzylidene-8,9-methylene-1,2,3,4,-tetrahydro-11-oxo-11H-pyrido[2,1-b]quinazoline-8-carboxylic acid;

4-benzylidene-1,2,3,4-tetrahydro-11-oxo-11H-pyrido[2,1-b]quinazoline-8-carboxylic acid, 2-(N,N-diethylamino)-ethyl ester;
4-benzylidene-8-methyl-1,2,3,4-tetrahydro-11H-pyrido[2,1-b]quinazoline-11-one; and
3-benzylidene-7-methyl-1,2,3,10-tetrahydro-cyclopenta[d]pyrido[1,2-a]pyrimidine-10-one; nd the pharmaceutically acceptable salts thereof, in particular the sodium salts and the hydrochlorides, the basic esters (e.g. those with 2-diethylamino-ethanol) and the $C_1$–$C_6$ alkyl esters thereof, in particular the methyl, ethyl, isopropyl, n-butyl and hexyl esters. The compounds of the invention can be prepared by a process comprising:

(a) reacting a compound of formula (II)

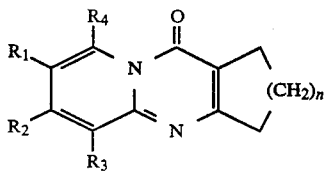

wherein
n, $R_1$, $R_2$, $R_3$, $R_4$ are as defined above or a salt thereof, with an aldehyde of formula (III)

    (III)

wherein
R is as defined above, so obtaining compounds of formula (I) wherein A is a bond; or (b) cyclopropanating a compound of formula (IV)

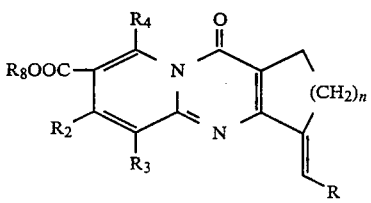

wherein
n, R, $R_2$, $R_3$, $R_4$ and $R_8$ are as defined above or a salt thereof, so obtaining compounds of formula (I) wherein $R_1$ is —$COOR_8$ wherein $R_8$ is as defined above and A is a —$CH_2$— group; and/or, if desired, converting a compound of formula (I) into another compound of formula (I) and/or, if desired, converting a compound of formula (I) into a pharmaceutically acceptable salt and/or, if desired, converting a salt into a free compound and/or, if desired, separating a mixture of isomers into the single isomers.

Preferred salts of a compound of formula (II) are, for example, those with inorganic bases such as sodium, potassium and calcium salts, as well as the salts with inorganic acids such as hydrochloric, hydrobromic and sulphuric acid.

The reaction of a compound of formula (II) with an aldehyde of formula (III) is preferably carried out in the presence of basic condensing agents such as, sodium ethoxide, sodium methoxide, sodium hydride, sodium amide, or potassium tert.butoxide, in a solvent such as methanol, ethanol, dioxane, tert.butanol or their mixtures at a temperature preferably ranging from about 0° C. to about 120° C.

Preferred salts of a compound of formula (IV) are, for example, those with inorganic bases such as sodium, potassium and calcium salts.

The cyclopropanation of a compound of formula (IV) may be carried out, for example, by reaction with dimethylsulphoxonium methylide (prepared e.g. according to the method described in J. Chem. Soc., 1967, 2495), operating in an inert organic solvent such as dimethylformamide, dimethylacetamide, dimethylsulphoxide or dioxane or their mixtures; the temperature ranges preferably from 0° C. to 50° C. and the reaction time is generally less than 5 hours, preferably less than 2 hours. Preferably 1–3 moles, in particular 1–1.5 moles, of the reagent are used for one mole of the compound of formula (IV).

A compound of formula (I) may be converted, as stated above, into another compound of formula (I) by known methods; for example, the compound of formula (I) wherein $R_1$ is an esterified carboxy group, may be converted into a compound of formula (I) wherein $R_1$ is carboxy by hydrolysis, e.g. basic hydrolysis, using, for example, sodium or potassium hydroxide, in a solvent, such as, water or a lower aliphatic alcohol, and operating at a temperature ranging from room temperature to 150° C.; the same reaction may be also carried out e.g. by treatment with lithium bromide in dimethylformamide at a temperature higher than 50° C. or by treatment with hydrochloric or hydrobromic or hydroiodic or sulphuric acid in acetic acid at a temperature higher than 50° C.

A compound of formula (I) wherein $R_1$ is a —COOH group may be converted into a compound of formula (I) wherein $R_1$ is a —$CONH_2$ group, for example, by reacting the compound of formula (I) wherein $R_1$ is carboxy with ethyl chlorocarbonate in the presence of triethylamine in a solvent such as benzene, toluene, dioxane, tetrahydrofurane or dichloroethane at a temperature ranging from 0° C. to 25° C., so obtaining the corresponding mixed anhydride, which in turn is reacted with gaseous ammonia in the same solvents at a temperature varying from about 0° C. to about 25° C.

A compound of formula (I) wherein $R_1$ is a —$CONH_2$ group may be converted into a compound of formula (I) wherein $R_1$ is a —CN group, by dehydrating the amide, e.g. by means of p-toluenesulphonyl chloride in pyridine and dimethylformamide at a temperature ranging from room temperature to about 100° C.

A compound of formula (I) wherein $R_1$ is carboxy may be converted into a compound of formula (I) wherein $R_1$ is an esterified carboxy group, e.g. a carbalkoxy group unsubstituted or substituted by a lower dialkylamino group, by conventional methods, for example by reacting an alkaline salt of the acid with a suitable alkyl halide, in an inert solvent, such as, acetone, dioxane, dimethylformamide or hexamethylphosphorotriamide at a temperature ranging from about 0° C. to about 100° C.

Alternatively a compound of formula (I) wherein $R_1$ is carboxy may be converted into a compound of formula (I) wherein $R_1$ is an esterified carboxy group, as defined above, by reaction with $SOCl_2$ in a solvent such as dioxane or dichloroethane at the reflux temperature so to obtain the corresponding chlorocarbonyl derivative, which in turn is reacted with a suitable alkyl alcohol in a solvent such as benzene, toluene, dioxane, dichloroethane, methylene chloride, chloroform at a temperature ranging from 0° C. to about 50° C.

Free hydroxy groups, as substituents in the phenyl ring may be, for example, etherified by reacting with a suitable alkyl halide in the presence of a base such as NaOH, KOH, $Na_2CO_3$, $K_2CO_3$, NaH, $NaNH_2$, sodium methoxide or sodium ethoxide, in a solvent such as methanol, ethanol, dioxane, acetone, dimethylformamide, hexamethylphosphorotriamide, tetrahydrofurane or water or their mixtures at a temperature ranging preferably from 0° C. to about 150° C.

Furthermore the etherified hydroxy groups may be converted into free hydroxy groups, for example, by treatment with pyridine hydrochloride or with a strong acid such as, HCl, HBr or HI, or with a Lewis acid such as, $AlCl_3$ or $BBr_3$.

Furthermore a free hydroxy or amino group, for example, may be converted respectively into a $C_2$–$C_8$ alkanoyloxy or $C_2$–$C_8$ alkanoylamino group using conventional methods well known in organic chemistry.

A nitro group as substituent on the phenyl ring may be converted into an amino group by treatment, for example, with stannous chloride in concentrated hydrochloric acid, using, if necessary, an organic cosolvent such as acetic acid, dioxane, tetrahydrofuran, at a temperature varying between room temperature and about 100° C.

Also the optional salification of a compound of formula (I) as well as the conversion of a salt into the free compound and the separation of a mixture of isomers into the single isomers may be carried out by conventional methods.

For example the separation of a mixture of optical isomers into the individual isomers may be carried out by salification with an optically active base and subsequent fractional crystallization.

The compounds of formula (II) may, for example, be prepared by reacting a compound of formula (V)

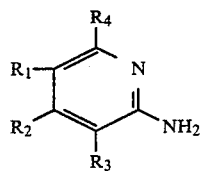

wherein
$R_1$, $R_2$, $R_3$ and $R_4$ are as defined above, with a compound of formula (VI)

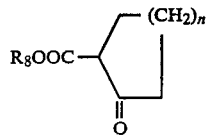

wherein
n and $R_8$ are as defined above. The reaction between a compound of formula (V) and a compound of formula (VI) may, for example, be carried out in the presence of an acid condensing agent such as polyphosphoric acid (polyphosphoric acid means a mixture of equal weights of 99% $H_3PO_4$ and $P_2O_5$), sulphuric acid, methanesulphonic acid, p-toluene sulphonic acid, at a temperature from 50° C. to 150° C.; the reaction may be carried out in an organic solvent such as dimethylformamide, dimethylacetamide, acetic acid, formic acid, benzene, toluene, xylene or ethylene glycol monomethylether, but it is preferably carried out in the absence of a solvent.

The compounds of formula (IV) may, for example, be prepared by reacting a compound of formula (VII)

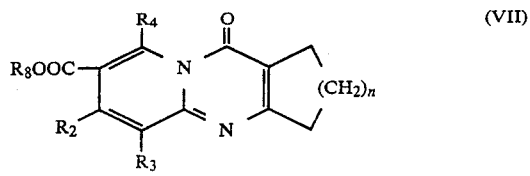

wherein
n, $R_2$, $R_3$, $R_4$ and $R_8$ are as defined above, and an aldehyde of formula (III), using the same experimental conditions defined above for the reaction between a compound of formula (II) and an aldehyde of formula (III).

The compounds of formula (VII) may be, for example, prepared by reacting a compound of formula (VIII)

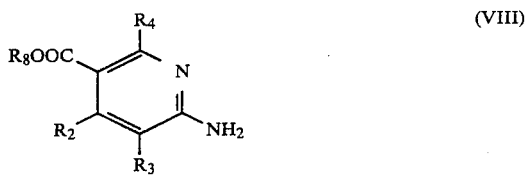

wherein
$R_2$, $R_3$, $R_4$ and $R_8$ are as defined above, with a compound of formula (VI), using the same experimental conditions defined above for the reaction between a compound of formula (V) and a compound of formula (VI).

The compounds of formula (III), (V), (VI) and (VIII) are known compounds and may be prepared by conventional methods: in some cases they are commercially available products.

The compounds of this invention are useful for the prevention and the treatment of all the diseases in which inflammatory and/or anaphylactic mediators are involved, for example, the allergic affections and the inflammatory diseases.

Therefore the compounds of this invention are useful in the prevention and treatment, e.g., of allergic rhinitis, hay fever, urticaria, dermatitis and particularly are effective in the prevention and treatment of the allergic bronchial asthma.

Furthermore the compounds of this invention are useful also in the treatment, e.g., of rheumatoid arthritis and osteoarthrosis.

The activity of the compounds of this invention is shown, e.g. by the fact that they are active in the following biological tests: in vitro (1) test of A 23187 induced SRS production from rat peritoneal cells, according to M. K. Bach and J. R. Brashler (J. Immunol., 113, 2040, 1974);

(2) test of antigen induced SRS production from chopped guinea-pig lung, according to W. E. Brocklehurst (J. Physiol., 151, 416, 1960); and in vivo (3) test of the IgG mediated passive peritoneal anaphylaxis in the rat, according to H. C. Morse, K. J. Bloch and K. F. Austen (Journal Immunology, 101, 658, 1968); and (4) test of the IgE mediated passive cutaneous anaphylaxis (PCA) in the rat, according to A. M. J. N. Blair (Immunology, 16, 749, 1969).

The results of these biological tests show that the compounds of the invention are active, for example, as inhibitors of the immunological release of mediators, e.g. histamine, from the mast cells and as inhibitors of the production and/or release of anaphylactic mediators such as "slow reacting substances" (SRS) in the peritoneal and in the pulmonary system, induced by challenge with an ionophore or with an antigen.

As preferred example of compound having antiallergic activity the following can be mentioned:
4-benzylidene-1,2,3,4-tetrahydro-11-oxo-11H-pyrido[2,1-b]quinazoline-8-carboxylic acid (internal code FCE 21273).

The following Table I shows, for example, the in vitro inhibition obtained by the compound FCE 21273 of the SRS production from rat peritoneal cells and from chopped guinea-pig lung.

TABLE I

| Sensitized system | FCE 21273 mcg/ml | Inhibition of SRS production |
| --- | --- | --- |
| Rat peritoneal cells | 1 | 50% |
| Chopped guinea-pig lung | 10 | 47% |

Furthermore the compounds of this invention are effective in vivo, for example, in inhibiting the Reversed Passive Arthus Reaction (RPAR) which is a model of immune-complex induced inflammatory reaction initiated by the interaction of antigen and antibody resulting in the formation of precipitating immune-complex, followed by complement fixation and accumulation of PMN in the focal site (D. K. Gemmell, J. Cottney and A. J. Lewis, Agents and Actions 9/1 page 107, 1979).

For example, in the above test in the rat the compound FCE 21273 gives about a 30% inhibition of RPAR reaction when administered orally at a dosage of 100 mg/kg. The compounds of the present invention, furthermore, are active on the gastroenterical system, in particular they are endowed with anti-ulcerogenic and anti-secretory activity and are therefore useful in therapy, for example, in the prevention and treatment of peptic, e.g., duodenal, gastric and esophageal, ulcers and to inhibit gastric acid secretion. The anti-ulcerogenic activity of the compounds of the invention is shown, e.g., by the fact that they are active in the test of inhibition of restraint ulcers in rats, according to the method of Bonfils et al. (Thérapie, 1960, 15, 1096; Jap. J.Pharmac. 1968, 18, 9). The following Table shows, for example, the approximate $ED_{50}$ value of the anti-ulcerogenic activity in the rat obtained for one of the compounds of the invention after oral administration:

TABLE

| Compound | Anti-ulcerogenic activity |
| --- | --- |
| 3-benzylidene-1,2,3,10-tetra hydro-10-oxo-10H—cyclopenta [d]pyrido[1,2-a]pyrimidine 7-carboxylic acid | $ED_{50} = 12$ mg/kg |

The tested compound was administered per os (p.o.) one hour before the immobilization.

Six Sprague-Dawley male rats (100–120 g) fasted 24 hours were used for the experiment: a square flexible small-mesh wire netting was used for the immobilization and 4 hours after the immobilization the rats were sacrificed, their stomachs were removed and the lesions counted under a dissecting microscope.

The compounds of the invention own also antisecretory activity as shown by the fact that after intraduodenal administration, they proved to be active in inhibiting the gastric secretion in rats according to the method of H. Shay et al. (Gastroenter., 1945, 43, 5).

One of the preferred compounds of the invention having antisecretory activity is, for example, the compound 3-(2-methyl-benzylidene)-1,2,3,10-tetrahydro-10-oxo-10H-cyclopenta[d]pyrido[1,2-a]pyrimidine-7-carboxylic acid, which has an approximate $ED_{25}$ value of 10 mg/kg in the above test in the rat, after intraduodenal administration. In view of their high therapeutic index the compounds of the invention can be safely used in medicine. For example, the approximate acute toxicity ($LD_{50}$) of the compounds 3-benzylidene-1,2,3,10-tetrahydro-10-oxo-cyclopenta[d]pyrido[1,2-a]pyrimidine-7-carboxylic acid, 3-(2-methyl-benzylidene)-1,2,3,10-tetrahydro-10-oxo-10H-cyclopenta[d]pyrido[1,2-a]pyrimidine-7-carboxylic acid and 4-benzylidene-1,2,3,4-tetrahydro-11-oxo-11H-pyrido[2,1-b]quinazoline-8-carboxylic acid, in the mouse, determined with single administration of increasing doses and measured on the seventh day after the day of treatment, is per os higher than 800 mg/kg. Analogous toxicity data have been found for the other compounds of the invention.

The dosage depends on the age, weight, conditions of the patient and administration route; for example, the dosage adopted for oral administration to adult humans may range from about 50 to about 200 mg pro dose, from 1 to 5 times daily. The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form, e.g., in the form of aqueous or oily solutions or suspensions, aerosols, as well as powders, tablets, pills, gelatine capsules, syrups, drops, suppositories, or creams, or lotions for topical use. Thus, for oral administration, the pharmaceutical compositions containing the compounds of this invention, are preferably tablets, pills or gelatine capsules which contain the active substance together with diluents, such as lactose, dextrose, sucrose, mannitol, sorbitol, cellulose; lubricants, for instance, silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents such as lecithin, polisorbates, laurylsulphates; and, in general, non-toxic and pharmacologically inactive substances used in pharmaceutical formulations.

Said pharmaceutical preparations may be manufactured in known manner, for example, by means of mixing, granulating, tabletting, sugar-coating, or film-coating processes. For the treatment of allergic asthma, the compounds of the invention are also administered by inhalation. For such use, suitable compositions may comprise a suspension or solution of the active ingredient, preferably in the form of a salt, such as the sodium salt or the salt with triethanolamine or with tris-(hydroxymethyl)-aminomethane, in water, for administration by means of a conventional nebulizer.

Alternatively, the compositions may comprise a suspension or a solution of the active ingredient in a conventional liquified propellant, such as dichlorodifluoromethane or dichlorotetrafluoroethane to be administered from a pressurized container, i.e., an aerosol dispenser. When the medicament is not soluble in the propellant, it may be necessary to add a co-solvent, such as, ethanol, dipropylene glycol, isopropyl myristate, and/or surface-active agent to the composition, in order to suspend the medicament in the propellant medium and such surface-active agents may be any of those commonly used for this purpose, such as non-ionic surface-active agents, e.g., lecithin.

The compounds of the invention may also be administered in the form of powders by means of a suitable insufflator device and in this case the fine particle sized powders of the active ingredients may be mixed with a diluent material such a lactose.

Furthermore, the compounds of this invention may also be administered by intradermal or intravenous injection in the conventional manner.

In addition to the internal administration, the compounds of this invention may find use in compositions for topical application, e.g. as creams lotions or pastes for use in dermatological treatments.

For these compositions the active ingredient may be mixed with conventional oleaginous or emulsifying excipients.

The following examples illustrate but do not limit the present invention.

EXAMPLE 1

2-amino-5-chloro-pyridine (3.8 g) was reacted with ethyl-2-oxo-cyclopentanecarboxylate (9.2 g) in the presence of polyphosphoric acid (38 g, obtained from 18.1 g of $P_2O_5$ and 19.9 g of 99% $H_3PO_4$) under stirring at 100° C. for one hour. After cooling the reaction mixture was diluted in ice-water and neutralized to pH=6 using 35% sodium hydroxide.

The precipitate was filtered and crystallized from ethyl acetate to give 7-chloro-1,2,3,10-tetrahydro-cyclopenta[d]pyrido[1,2-a]pyrimidine-10-one, m.p. 146°–147° (3.5 g), which was reacted with benzaldehyde (6.7 g) in methanol (140 ml) in the presence of sodium methoxide (3.38 g) under stirring at reflux temperature for 68 hours. After cooling the precipitate was filtered, washed with water until neutral and crystallized from $CH_2Cl_2$/acetone to give 3.12 g of 3-benzylidene-7-chloro-1,2,3,10-tetrahydro-cyclopenta[d]pyrido[1,2-a]pyrimidine-10-one, m.p. 212°–213° C., NMR ($CF_3COOD$) δ ppm: 3.40 (br s) (4H, C-1 and C-2 cyclopentane protons), 7.39 (m) (6H, phenyl and methine protons), 8.27 (d) (1H, C-5 proton), 8.50 (d.d) (1H, C-6 proton), 9.47 (d) (1H, C-8 proton).

By proceeding analogously, starting from suitable halogenated 2-amino-pyridines, the following compounds were prepared:
3-benzylidene-7-bromo-1,2,3,10-tetrahydro-cyclopenta[d]-pyrido[1,2-a]pyrimidine-10-one, m.p. 225°–226° C.;
3-benzylidene-5,7-dichloro-1,2,3,10-tetrahydro-cyclopenta[d]pyrido[1,2-a]pyrimidine-10-one, m.p. 248°–250° C.; and
3-benzylidene-5,7-dibromo-1,2,3,10-tetrahydro-cyclopenta[d]pyrido[1,2-a]pyrimidine-10-one.

EXAMPLE 2

7-chloro-1,2,3,10-tetrahydro-cyclopenta[d]pyrido[1,2-a]pyrimidine-10-one (4 g), prepared according to Example 1, was reacted with 3,4,5-trimethoxy-benzaldehyde (8,87 g) in methanol (160 ml) in the presence of sodium methoxide (1.65 g) at reflux temperature for 140 hours. After cooling the precipitate was filtered, washed with water until neutral and crystallized from $CH_2Cl_2$/methanol to give 4.4 g of 7-chloro-3-(3,4,5-trimethoxy-benzylidene)-1,2,3,10-tetrahydro-cyclopenta[d]pyrido[1,2-a]pyrimidine-10-one, m.p. 222°–223° C., NMR ($CDCl_3$) δ ppm: 3.13 (br s) (4H, cyclopentane protons), 3.95 (br s) (9H, —$OCH_3$), 6.82 (s) (2H, phenyl protons), 7.42 (br s) (1H, =CH—), 7.58 (d) (2H, C-5 and C-6 protons), 9.02 (t) (1H, C-8 proton).

By proceeding analogously the following compounds were prepared:
7-chloro-3-(2-methoxy-benzylidene)-1,2,3,10-tetrahydro-cyclopenta[d]pyrido[1,2-a]pyrimidine-10-one, m.p. 236°–237° C;
7-chloro-3-(3-methoxy-benzylidene)-1,2,3,10-tetrahydro-cyclopenta[d]pyrido[1,2-a]pyrimidine-10-one, m.p. 206°–207° C.;
7-chloro-3-(4-methoxy-benzylidene)-1,2,3,10-tetrahydro-cyclopenta[d]pyrido[1,2-a]pyrimidine-10-one, m.p. 257°–258° C.;
7-chloro-3-(2,3-dimethoxy-benzylidene)-1,2,3,10-tetrahydro-cyclopenta[d]pyrido[1,2-a]pyrimidine-10-one, m.p. 234°–245° C.;
7-chloro-3-(2,5-dimethoxy-benzylidene)-1,2,3,10-tetrahydro-cyclopenta[d]pyrido[1,2-a]pyrimidine-10-one;
7-chloro-3-(3,4-dimethoxy-benzylidene)-1,2,3,10-tetrahydro-cyclopenta[d]pyrido[1,2-a]pyrimidine-10-one;
7-chloro-3-(3,4-methylenedioxy-benzylidene)-1,2,3,10-tetrahydro-cyclopenta[d]pyrido[1,2-a]pyrimidine-10-one;
7-chloro-3-(2,3,4-trimethoxy-benzylidene)-1,2,3,10-tetrahydro-cyclopenta[d]pyrido[1,2-a]pyrimidine-10-one, m.p. 222°–224° C.;
7-chloro-3-(2-methyl-benzylidene)-1,2,3,10-tetrahydro-cyclopenta[d]pyrido[1,2-a]pyrimidine-10-one, m.p. 261°–262° C.;
7-chloro-3-(4-methyl-benzylidene)-1,2,3,10-tetrahydro-cyclopenta[d]pyrido[1,2-a]pyrimidine-10-one, m.p. 235°–237° C.;
7-chloro-3-(2-methoxy-3-ethoxy-benzylidene)-1,2,3,10-tetrahydro-cyclopenta[d]pyrido[1,2-a]pyrimidine-10-one;
7-chloro-3-(2-ethoxy-3-methoxy-benzylidene)-1,2,3,10-tetrahydro-cyclopenta[d]pyrido[1,2-a]pyrimidine-10-one;
7-bromo-3-(2,3-dimethoxy-benzylidene)-1,2,3,10-tetrahydro-cyclopenta[d]pyrido[1,2-a]pyrimidine-10-one;
7-chloro-3-(2,3-diethoxy-benzylidene)-1,2,3,10-tetrahydro-cyclopenta[d]pyrido[1,2-a]pyrimidine-10-one;
5,7-dichloro-3-(2-methoxy-3-ethoxy-benzylidene)-1,2,3,10-tetrahydro-cyclopenta[d]pyrido[1,2-a]pyrimidine-10-one;
5,7-dichloro-3-(2-ethoxy-3-methoxy-benzylidene)-1,2,3,10-tetrahydro-cyclopenta[d]pyrido[1,2-a]pyrimidine-10-one;
5,7-dichloro-3-(2,3-dimethoxy-benzylidene)-1,2,3,10-tetrahydro-cyclopenta[d]pyrido[1,2-a]pyrimidine-10-one; and 7-chloro-3-(2,4-dimethoxy-benzylidene)-1,2,3,10-tetrahydro-cyclopenta[d]pyrido[1,2-a]pyrimidine-10-one.

EXAMPLE 3

-chloro-1,2,3,10-tetrahydro-cyclopenta[d]pyrido[1,2-a]pyrimidine-10-one (3.5 g), prepared according to Example 1, was reacted with 2-chlorobenzaldehyde (3.4 g) in methanol (150 ml) in the presence of sodium methoxide (1.73 g) under stirring at reflux temperature for 36 hours.

After cooling the precipitate was filtered, washed with water until neutral and crystallized from chloroform to give 3 g of 7-chloro-3-(2-chloro-benzylidene)-1,2,3,10-tetrahydro-cyclopenta[d]pyrido[1,2-a]pyrimidine-10-one, m.p. 249°–250° C., NMR (CF$_3$COOD) δ ppm: 3.34 (s) (4H, C-1 and C-2 protons), 7.45 (m) (3H, 3-,4- and 5-phenyl protons), 7.70 (m) (1H, 6-phenyl proton), 7.91 (m) (1H, =CH—), 8.25 (d) (1H, C-5 proton), 8.50 (d.d) (1H, C-6 proton), 9.48 (d) (1H, C-8 proton).

By proceeding analogously, reacting suitable halogenated 1,2,3,10-tetrahydro-cyclopenta[d]pyrido[1,2-a]pyrimidines with suitable substituted benzaldehydes, the following compounds were prepared:

7-chloro-3-(3-chloro-benzylidene)-1,2,3,10-tetrahydro-cyclopenta[d]pyrido[1,2-a]pyrimidine-10-one, m.p. 270°–272° C.;

7-chloro-3-(4-chloro-benzylidene)-1,2,3,10-tetrahydro-cyclopenta[d]pyrido[1,2-a]pyrimidine-10-one, m.p. 253°–256° C.;

7-chloro-3-(2,6-dichloro-benzylidene)-1,2,3,10-tetrahydro-cyclopenta[d]pyrido[1,2-a]pyrimidine-10-one, m.p. 234°–236° C.;

7-chloro-3-(2,4-dichloro-benzylidene)-1,2,3,10-tetrahydro-cyclopenta[d]pyrido[1,2-a]pyrimidine-10-one, m.p. 298°–300° C.;

7-chloro-3-(3,4-dichloro-benzylidene)-1,2,3,10-tetrahydro-cyclopenta[d]pyrido[1,2-a]pyrimidine-10-one, m.p. 279°–280° C.;

7-bromo-3-(2-chloro-benzylidene)-1,2,3,10-tetrahydro-cyclopenta[d]pyrido[1,2-a]pyrimidine-10-one;

7-bromo-3-(3-chloro-benzylidene)-1,2,3,10-tetrahydro-cyclopenta[d]pyrido[1,2-a]pyrimidine-10-one;

7-bromo-3-(4-chloro-benzylidene)-1,2,3,10-tetrahydro-cyclopenta[d]pyrido[1,2-a]pyrimidine-10-one;

7-bromo-3-(2,6-dichloro-benzylidene)-1,2,3,10-tetrahydro-cyclopenta[d]pyrido[1,2-a]pyrimidine-10-one, m.p. 233°–234° C.;

7-bromo-3-(2,4-dichloro-benzylidene)-1,2,3,10-tetrahydro-cyclopenta[d]pyrido[1,2-a]pyrimidine-10-one;

5,7-dichloro-3-(2,6-dichloro-benzylidene)-1,2,3,10-tetrahydro-cyclopenta[d]pyrido[1,2-a]pyrimidine-10-one, m.p. 164°–166° C.;

5,7-dichloro-3-(2-chloro-benzylidene)-1,2,3,10-tetrahydro-cyclopenta[d]pyrido[1,2-a]pyrimidine-10-one;

5,7-dichloro-3-(3-chloro-benzylidene)-1,2,3,10-tetrahydro-cyclopenta[d]pyrido[1,2-a]pyrimidine-10-one;

5,7-dichloro-3-(4-chloro-benzylidene)-1,2,3,10-tetrahydro-cyclopenta[d]pyrido[1,2-a]pyrimidine-10-one;

7-chloro-3-(4-fluoro-benzylidene)-1,2,3,10-tetrahydro-cyclopenta[d]pyrido[1,2-a]pyrimidine-10-one;

7-bromo-3-(4-fluoro-benzylidene)-1,2,3,10-tetrahydro-cyclopenta[d]pyrido[1,2-a]pyrimidine-10-one;

5,7-dichloro-3-(4-fluoro-benzylidene)-1,2,3,10-tetrahydro-cyclopenta[d]pyrido[1,2-a]pyrimidine-10-one;

5,7-dibromo-3-(4-fluoro-benzylidene)-1,2,3,10-tetrahydro-cyclopenta[d]pyrido[1,2-a]pyrimidine-10-one;

7-chloro-3-(4-N,N-dimethylamino-benzylidene)-1,2,3,10-tetrahydro-cyclopenta[d]pyrido[1,2-a]pyrimidine-10-one;

7-bromo-3-(4-N,N-dimethylamino-benzylidene)-1,2,3,10-tetrahydro-cyclopenta[d]pyrido[1,2-a]pyrimidine-10-one; and 5,7-dichloro-3-(4-N,N-dimethylamino-benzylidene)-1,2,3,10-tetrahydro-cyclopenta[d]pyrido[1,2-a]pyrimidine-10-one.

EXAMPLE 4

1,2,3,10-tetrahydro-10-oxo-cyclopenta[d]pyrido[1,2-a]pyrimidine-7-carboxylic acid methyl ester, m.p. 153°–154° C. (3.3 g) was reacted with 3-methoxybenzaldehyde (5.52 g) in methanol (145 g) in the presence of sodium methoxide (2.97 g) under stirring at reflux temperature for 144 hours. After cooling the precipitate was filtered and treated with formic acid and then with water: the crude compound was recovered by filtration, washed with water until neutral and crystallized from CH$_2$Cl$_2$/methanol to give 2.73 g of 3-(3-methoxy-benzylidene)-1,2,3,10-tetrahydro-10-oxo-cyclopenta[d]pyrido[1,2-a]pyrimidine-7-carboxylic acid, m.p. 310°–312° C., NMR (CF$_3$COOD) δ ppm: 3.42 (br) (4H, cyclopentane protons), 4.11 (s) (3H, OCH$_3$), 7.2–7.6 (m) (4H, phenyl protons), 7.61 (br) (1H, =CH—), 8.41 (d) (1H, C-5 proton), 9.11 (d.d) (1H, C-6 proton), 10.20 (d) (1H, C-8 proton).

By proceeding analogously the following compounds were prepared:

3-(2-methoxy-benzylidene)-1,2,3,10-tetrahydro-10-oxo-cyclopenta[d]pyrido[1,2-a]pyrimidine-7-carboxylic acid, m.p. 322°–324° C.;

3-(4-methoxy-benzylidene)-1,2,3,10-tetrahydro-10-oxo-cyclopenta[d]pyrido[1,2-a]pyrimidine-7-carboxylic acid, m.p. 368°–370° C.

3-(2-ethoxy-benzylidene)-1,2,3,10-tetrahydro-10-oxo-cyclopenta[d]pyrido[1,2-a]pyrimidine-7-carboxylic acid;

3-(2,3-dimethoxy-benylidene)-1,2,3,10-tetrahydro-10-oxo-cyclopenta[d]pyrido[1,2-a]pyrimidine-7-carboxylic acid, m.p. 309°–311° C.;

3-(3-ethoxy-benzylidene)-1,2,3,10-tetrahydro-10-oxo-cyclopenta[d]pyrido[1,2-a]pyrimidine-7-carboxylic acid, m.p. 328°–332° C.;

3-(2,5-dimethoxy-benzylidene)-1,2,3,10-tetrahydro-10-oxo-cyclopenta[d]pyrido[1,2-a]pyrimidine-7-carboxylic acid; and 3-(3,4-dimethoxy-benzylidene)-1,2,3,10-tetrahydro-10-oxo-cyclopenta[d]pyrido[1,2-a]pyrimidine-7-carboxylic acid.

EXAMPLE 5

1,2,3,10-tetrahydro-10-oxo-cyclopenta[d]pyrido[1,2-a]pyrimidine-7-carboxylic acid methyl ester, m.p. 153°–154° C. (5 g) in methanol (300 ml) containing 6.45 g of sodium methoxide was reacted with 10.9 g of benzaldehyde under stirring at reflux temperature for 96 hours. After cooling and concentration in vacuo to a small volume the precipitate was filtered and treated with acetic acid and then with water; the crude compound was recovered by filtration, washed with water until neutral and crystallized from CH$_2$Cl$_2$/methanol and then from dioxane to give 3.25 g of 3-benzylidene-1,2,3,10-tetrahydro-10-oxo-cyclopenta[d]pyrido[1,2-a]pyrimidine-7-carboxylic acid, m.p. 309°–310° C., NMR (CF$_3$COOD) δ ppm: 3.44 (m) (4H, cyclopentane protons), 7.68 (m) (6H, =CH— and phenyl protons), 8.44 (d) (1H, C-5 proton), 9.15 (d.d) (1H, C-6 proton), 10.23 (d) (1H, C-8 proton).

By proceeding analogously the following compounds were prepared:

3-(3-methyl-benzylidene)-1,2,3,10-tetrahydro-10-oxo-cyclopenta[d]pyrido[1,2-a]pyrimidine-7-carboxylic acid;

3-(4-methyl-benzylidene)-1,2,3,10-tetrahydro-10-oxo-cyclopenta[d]pyrido[1,2-a]pyrimidine-7-carboxylic acid;

3-(2,5-dimethyl-benzylidene)-1,2,3,10-tetrahydro-10-oxo-cyclopenta[d]pyrido[1,2-a]pyrimidine-7-carboxylic acid;

3-(2,4-dimethyl-benzylidene)-1,2,3,10-tetrahydro-10-oxo-cyclopenta[d]pyrido[1,2-a]pyrimidine-7-carboxylic acid;

3-(4-fluoro-benzylidene)-1,2,3,10-tetrahydro-10-oxo-cyclopenta[d]pyrido[1,2-a]pyrimidine-7-carboxylic acid;

3-(3-chloro-benzylidene)-1,2,3,10-tetrahydro-10-oxo-cyclopenta[d]pyrido[1,2-a]pyrimidine-7-carboxylic acid, m.p. 318°–320° C.;

3-(2-methyl-benzylidene)-1,2,3,10-tetrahydro-10-oxo-cyclopenta[d]pyrido[1,2-a]pyrimidine-7-carboxylic acid, m.p. 300°–302° C.;

3-(2,6-dichloro-benzylidene)-1,2,3,10-tetrahydro-10-oxo-cyclopenta[d]pyrido[1,2-a]pyrimidine-7-carboxylic acid, m.p. 292°–295° C.;

3-(2,4-dichloro-benzylidene)-1,2,3,10-tetrahydro-10-oxo-cyclopenta[d]pyrido[1,2-a]pyrimidine-7-carboxylic acid;

3-(3,4-dichloro-benzylidene)-1,2,3,10-tetrahydro-10-oxo-cyclopenta[d]pyrido[1,2-a]pyrimidine-7-carboxylic acid;

3-(4-N,N-dimethylamino-benzylidene)-1,2,3,10-tetrahydro-10-oxo-cyclopenta[d]pyrido[1,2-a]pyrimidine-7-carboxylic acid, m.p. 330°–340° C. dec.; and 3-(2-chloro-benzylidene)-1,2,3,10-tetrahydro-10-oxo-cyclopenta[d]pyrido[1,2-a]pyrimidine-7-carboxylic acid.

EXAMPLE 6

1,2,3,10-tetrahydro-10-oxo-cyclopenta[d]pyrido[1,2-a]pyrimidine-7-carboxylic acid (3.12 g) in methanol (145 ml) containing 2.9 g of sodium methoxide was reacted with 4.86 g of 2-methyl-benzaldehyde under stirring at reflux temperature for 144 hours. After cooling and concentration in vacuo to a small volume, the precipitate was filtered and treated with acetic acid and then with water: the crude compound was recovered by filtration, washed with water until neutral and crystallized from CH$_2$Cl$_2$/methanol and then from dioxane to give 1.9 g of 3-(2-methyl-benzylidene)-1,2,3,10-tetrahydro-10-oxo-cyclopenta[d]pyrido[1,2-a]pyrimidine-7-carboxylic acid, m.p. 300°–302° C., NMR (CF$_3$COOD) δ ppm: 2.49 (s) (3H, —CH$_3$), 3.36 (s) (4H, cyclopentane protons), 7.42 (m) (3H, phenyl protons), 7.64 (m) (1H, phenyl proton), 7.81 (bs) (1H, ═CH—), 8.40 (d) (1H, C-5 proton), 9.11 (d d) (1H, C-6 proton), 10.23 (d) (1H, C-8 proton).

By proceeding analogously the following compounds were prepared:

3-(4-ethoxy-benzylidene)-1,2,3,10-tetrahydro-10-oxo-cyclopenta[d]pyrido[1,2-a]pyrimidine-7-carboxylic acid;

3-(3,4-methylenedioxy-benzylidene)-1,2,3,10-tetrahydro-10-oxo-cyclopenta[d]pyrido[1,2-a]pyrimidine-7-carboxylic acid; and 3-(2,3,4-trimethoxy-benzylidene)-1,2,3,10-tetrahydro-10-oxo-cyclopenta[d]pyrido[1,2-a]pyrimidine-7-carboxylic acid.

EXAMPLE 7

3-(3-ethoxy-benzylidene)-1,2,3,10-tetrahydro-10-oxo-cyclopenta[d]pyrido[1,2-a]pyrimidine-7-carboxylic acid (2.7 g), prepared according to Example 4, was heated with 37% HCl (54 ml) in acetic acid (54 ml) under stirring at reflux temperature for 20 hours. After cooling the precipitate was filtered, washed with water and then treated with aqueous sodium acetate under stirring: filtration and crystallization of the precipitate from dimethylformamide gave 1.85 g of 3-(3-hydroxy-benzylidene)-1,2,3,10-tetrahydro-10-oxo-cyclopenta[d]pyrido[1,2-a]pyrimidine-7-carboxylic acid, m.p. >320° C.

EXAMPLE 8

7-methyl-1,2,3,10-tetrahydro-cyclopenta[d]pyrido[1,2-a]pyrimidine-10-one (5 g) was reacted with benzaldehyde (13.2 g) in methanol (200 ml) in the presence of sodium methoxide (6.8 g) at reflux temperature for 96 hours. After cooling and concentration in vacuo to a small volume the precipitate was filtered and washed with water until neutral; crystallization from CH$_2$Cl$_2$/methanol gave 3-benzylidene-7-methyl-1,2,3,10-tetrahydro-cyclopenta[d]pyrido[1,2-a]pyrimidine-10-one, m.p. 197°–199° C., NMR (CDCl$_3$) δ ppm: 2.45 (s) (3H, CH$_3$), 3.10 (bs) (4H, C-1 and C-2 protons), 7.2–7.7 (m) (8H, ═CH— and C-5 and C-6 and phenyl protons), 8.80 (bs) (1H, C-8 proton).

By proceeding analogously, the following compounds were prepared:

3-(3-methoxy-benzylidene)-7-methyl-1,2,3,10-tetrahydro-cyclopenta[d]pyrido[1,2-a]pyrimidine-10-one;

3-(2-methoxy-benzylidene)-7-methyl-1,2,3,10-tetrahydro-cyclopenta[d]pyrido[1,2-a]pyrimidine-10-one;

3-(4-methoxy-benzylidene)-7-methyl-1,2,3,10-tetrahydro-cyclopenta[d]pyrido[1,2-a]pyrimidine-10-one;

3-(2,6-dichloro-benzylidene)-7-methyl-1,2,3,10-tetrahydro-cyclopenta[d]pyrido[1,2-a]pyrimidine-10-one, m.p. 210°–211° C.;

3-(2-methyl-benzylidene)-7-methyl-1,2,3,10-tetrahydro-cyclopenta[d]pyrido[1,2-a]pyrimidine-10-one;

3-(3-methyl-benzylidene)-7-methyl-1,2,3,10-tetrahydro-cyclopenta[d]pyrido[1,2-a]pyrimidine-10-one, and 3-(4-methyl-benzylidene)-7-methyl-1,2,3,10-tetrahydro-cyclopenta[d]pyrido[1,2-a]pyrimidine-10-one.

EXAMPLE 9

5-methoxy-1,2,3,10-tetrahydro-cyclopenta[d]pyrido[1,2-a]pyrimidine-10-one, m.p. 212°–214° C., (4 g) was reacted with benzaldehyde (8 g) in methanol (150 ml) in the presence of sodium methoxide (4 g) at reflux temperature for 150 hours. After cooling and concentration in vacuo to a small volume the precipitate was filtered and washed with water until neutral: crystallization from dioxane gave 2.5 g of 3-benzylidene-5-methoxy-1,2,3,10-tetrahydro-cyclopenta[d]pyrido[1,2-a]pyrimidine-10-one, m.p. 229°–230° C., NMR (DMSO d6) δ ppm: 3.26 (bs) (4H, C-1 and C-2 protons), 4.20 (s) (3H, OCH$_3$), 7.5–7.9 (m) (8H, ═CH, C-6 and C-7 and phenyl protons), 8.90 (d.d) (1H, C-8 proton).

By proceeding analogously the following compounds were prepared:

3-(2-chlorobenzylidene)-5-methoxy-1,2,3,10-tetrahydro-cyclopenta[d]pyrido[1,2-a]pyrimidine-10-one; and 3-(2,6-dichlorobenzylidene)-5-methoxy-1,2,3,10-tetrahydro-cyclopenta[d]pyrido[1,2-a]pyrimidine-10-one, m.p. 247°-248° C.

EXAMPLE 10

Trimethyl-sulphoxonium iodide (1.8 g) was reacted with 50% sodium hydride (0.39 g) in dimethyl formamide (30 ml) under stirring at room temperature for 60 minutes, then a solution of 3-benzylidene-1,2,3,10-tetrahydro-10-oxo-cyclopenta[d]pyrido[1,2-a]pyrimidine-7-carboxylic acid methyl ester, m.p. 248°-250° C., (2.49 g) in dimethylformamide (30 ml) was added. The mixture was allowed to react at room temperature for 1 hour then it was diluted with ice water and neutralized with acetic acid. The precipitate was filtered and washed with water to give 2.55 g of 3-benzylidene-7,8-methylene-1,2,3,10-tetrahydro-10-oxo-cyclopenta[d]pyrido[1,2-a]pyrimidine-7-carboxylic acid methyl ester, m.p. 185°-187° C., which was treated with 0.5% KOH in 95% ethanol solution (90 ml) at reflux temperature for 15 minutes. After cooling the reaction mixture was acidified with acetic acid and diluted with water: the precipitate was filtered, washed with water until neutral and crystallized from $CH_2Cl_2$/methanol to give 1.8 g of 3-benzylidene-7,8-methylene-1,2,3,10-tetrahydro-10-oxo-cyclopenta[d]pyrido[1,2-a]pyrimidine-7-carboxylic acid, m.p. 230°-240° C. dec., NMR ($CF_3COOD$) δ ppm: 1.19 (t) (1H, 7,8-methylene proton), 2.91 (d d) (1H, 7,8-methylene proton), 3.32 (br s) (4H, cyclopentane protons), 3.51 (d.d.) (1H, C-8 proton), 7.01 (d) (1H, C-5 proton), 7.45 (m) (1H, =CH—), 7.58 (br s) (5H, phenyl protons), 8.26 (d) (1H, C-6 proton).

By proceeding analogously the following compounds were prepared:

3-(2-methyl-benzylidene)-7,8-methylene-1,2,3,10-tetrahydro-10-oxo-cyclopenta[d]pyrido[1,2-a]pyrimidine-7-carboxylic acid, m.p. 254°-256° C.;

3-(2-methoxy-benzylidene)-7,8-methylene-1,2,3,10-tetrahydro-10-oxo-cyclopenta[d]pyrido[1,2-a]pyrimidine-7-carboxylic acid;

3-(3-methoxy-benzylidene)-7,8-methylene-1,2,3,10-tetrahydro-10-oxo-cyclopenta[d]pyrido[1,2-a]pyrimidine-7-carboxylic acid;

3-(4-methoxy-benzylidene)-7,8-methylene-1,2,3,10-tetrahydro-10-oxo-cyclopenta[d]pyrido[1,2-a]pyrimidine-7-carboxylic acid;

3-(2,3-dimethoxy-benzylidene)-7,8-methylene-1,2,3,10-tetrahydro-10-oxo-cyclopenta[d]pyrido[1,2-a]pyrimidine-7-carboxylic acid;

3-(4-fluoro-benzylidene)-7,8-methylene-1,2,3,10-tetrahydro-10-oxo-cyclopenta[d]pyrido[1,2-a]pyrimidine-7-carboxylic acid;

3-(3-methyl-benzylidene)-7,8-methylene-1,2,3,10-tetrahydro-10-oxo-cyclopenta[d]pyrido[1,2-a]pyrimidine-7-carboxylic acid;

3-(4-methyl-benzylidene)-7,8-methylene-1,2,3,10-tetrahydro-10-oxo-cyclopenta[d]pyrido[1,2-a]pyrimidine-7-carboxylic acid; and 3-(2-ethoxy-benzylidene)-7,8-methylene-1,2,3,10-tetrahydro-10-oxo-cyclopenta[d]pyrido[1,2-a]pyrimidine-7-carboxylic acid.

EXAMPLE 11

3-benzylidene-1,2,3,10-tetrahydro-10-oxo-cyclopenta[d]pyrido[1,2-a]pyrimidine-7-carboxylic acid (3.2 g) suspended in dioxane (70 ml) and tetrahydrofurane (30 ml) was reacted with ethyl chlorocarbonate (4.55 g) in the presence of triethylamine (4.05 g) under stirring at 15° C. for 2 hours. Then the reaction mixture was treated with dioxane (200 ml) saturated with gaseous ammonia for 30 minutes under stirring. After dilution with ice water and neutralization with HCl, the precipitate was filtered and purified by washing with dimethylformamide to give 2.52 g of 3-benzylidene-1,2,3,10-tetrahydro-10-oxo-cyclopenta[d]pyrido[1,2-a]pyrimidine-7-carboxamide, m.p. 350°-357° C., NMR ($CF_3COOD$) δ ppm: 3.40 (bs) (4H, C-1 and C-2 protons), 7.60 (m) (6H, =CH— and phenyl protons), 8.42 (d) (1H, C-5 proton), 9.03 (d d) (1H, C-6 proton), 10.09 (d) (1H, C-8 proton).

EXAMPLE 12

3-benzylidene-1,2,3,10-tetrahydro-10-oxo-cyclopenta[d]pyrido[1,2-a]pyrimidine-7-carboxamide (1.9 g) was reacted with p-toluensulphonyl chloride (2.28 g) in dimethylformamide (80 ml) in the presence of pyridine (2 ml) under stirring at room temperature for 24 hours. Dilution with ice water gave a precipitate which was filtered and crystallized with $CH_2Cl_2$/isopropyl ether to give 1.25 g of 3-benzylidene-7-cyano-1,2,3,10-tetrahydro-cyclopenta[d]pyrido[1,2-a]pyrimidine-10-one, m.p. 285°-287° C., NMR ($CF_3COOD/CDCl_3$) δ ppm: 3.34 (bs) (4H, C-1 and C-2 protons), 7.52 (bs) (6H, =CH— and phenyl protons), 8.45 (m) (2H, C-5 and C-6 protons), 9.76 (bs) (1H, C-8 proton).

EXAMPLE 13

3-benzylidene-1,2,3,10-tetrahydro-10-oxo-cyclopenta[d]pyrido[1,2-a]pyrimidine-7-carboxylic acid (1 g) was reacted with ethyl iodide (3.75 g) and anhydrous $K_2CO_3$ (3.3 g) in dimethylformamide (10 ml) under stirring at 100° C. for 72 hours. After cooling and dilution with ice water the precipitate was filtered and washed with water until neutral: 0.9 g of 3-benzylidene-1,2,3,10-tetrahydro-10-oxo-cyclopenta[d]pyrido[1,2-a]pyrimidine-7-carboxylic acid, ethyl ester, m.p. 225°-227° C., were obtained.

By proceeding analogously the following compounds were prepared:

3-(2-methoxy-benzylidene)-1,2,3,10-tetrahydro-10-oxo-cyclopenta[d]pyrido[1,2-a]pyrimidine-7-carboxylic acid, ethyl ester;

4-(3-methoxy-benzylidene)-1,2,3,10-tetrahydro-10-oxo-cyclopenta[d]pyrido[1,2-a]pyrimidine-7-carboxylic acid, ethyl ester;

3-(2,3-dimethoxy-benzylidene)-1,2,3,10-tetrahydro-10-oxo-cyclopenta[d]pyrido[1,2-a]pyrimidine-7-carboxylic acid, ethyl ester;

3-(4-fluoro-benzylidene)-1,2,3,10-tetrahydro-10-oxo-cyclopenta[d]pyrido[1,2-a]pyrimidine-7-carboxylic acid, ethyl ester;

3-benzylidene-7,8-methylene-1,2,3,10-tetrahydro-10-oxo-cyclopenta[d]pyrido[1,2-a]pyrimidine-7-carboxylic acid, ethyl ester;

3-(4-methoxy-benzylidene)-1,2,3,10-tetrahydro-10-oxo-cyclopenta[d]pyrido[1,2-a]pyrimidine-7-carboxylic acid, ethyl ester; and 3-(2-methyl-benzylidene)-1,2,3,10-tetrahydro-10-oxo-cyclopenta[d]pyrido[1,2-a]pyrimidine-7-carboxylic acid, ethyl ester.

EXAMPLE 14

3-benzylidene-1,2,3,10-tetrahydro-10-oxo-cyclopenta[d]pyrido[1,2-a]pyrimidine-7-carboxylic acid was treated with the stoichiometric amount of sodium methoxide in methanol at 60° C. for 10 minutes.

After concentration in vacuo to a small volume the precipitate was filtered and washed with a little amount of cold methanol and then with hexane: 3-benzylidene-1,2,3,10-tetrahydro-10-oxo-cyclopenta[d]pyrido[1,2-a]pyrimidine-7-carboxylic acid, sodium salt, m.p. >300° C. was obtained.

By proceeding analogously the following compounds were prepared:
3-(2-methoxy-benzylidene)-1,2,3,10-tetrahydro-10-oxo-cyclopenta[d]pyrido[1,2-a]pyrimidine-7-carboxylic acid, sodium salt;
3-(3-methoxy-benzylidene)-1,2,3,10-tetrahydro-10-oxo-cyclopenta[d]pyrido[1,2-a]pyrimidine-7-carboxylic acid, sodium salt;
3-(4-methoxy-benzylidene)-1,2,3,10-tetrahydro-10-oxo-cyclopenta[d]pyrido[1,2-a]pyrimidine-7-carboxylic acid, sodium salt;
3-(4-fluoro-benzylidene)-1,2,3,10-tetrahydro-10-oxo-cyclopenta[d]pyrido[1,2-a]pyrimidine-7-carboxylic acid, sodium salt;
3-benzylidene-7,8-methylene-1,2,3,10-tetrahydro-10-oxo-cyclopenta[d]pyrido[1,2-a]pyrimidine-7-carboxylic acid, sodium salt;
3-(2-methyl-benzylidene)-1,2,3,10-tetrahydro-10-oxo-cyclopenta[d]pyrido[1,2-a]pyrimidine-7-carboxylic acid, sodium salt, and
3-(2,3-dimethoxy-benzylidene)-1,2,3,10-tetrahydro-10-oxo-cyclopenta[d]pyrido[1,2-a]pyrimidine-7-carboxylic acid, sodium salt.

EXAMPLE 15

1,2,3,4-tetrahydro-11-oxo-11H-pyrido[2,1-b]quinazoline-8-carboxylic acid, methyl ester, m.p. 123°–124° C., (9 g), was reacted with benzaldehyde (11 g) in methanol (250 ml) in the presence of sodium methylate (7.3 g) under stirring at reflux temperature for 140 hours. After cooling the solution was concentrated in vacuo to a small volume; the precipitate was filtered and washed with little methanol and then dissolved in water.

Acidification with acetic acid gave a precipitate which was filtered, washed with water and dissolved in acetone: treatment with the stoichiometric amount of 37% HCl formed the sparingly soluble 4-benzylidene-1,2,3,4-tetrahydro-11-oxo-11H-pyrido[2,1-b]quinazoline-8-carboxylic acid, hydrochloride, m.p.>300° C., which was recovered by filtration and thoroughly washed with acetone.

Treatment with aqueous potassium carbonate to obtain the free compound and then crystallization from CH₂Cl₂-methanol gave 2.9 g of 4-benzylidene-1,2,3,4-tetrahydro-11-oxo-11H-pyrido[2,1-b]quinazoline-8-carboxylic acid, m.p. 261°–263° C., NMR (CF₃COOD) δppm: 2.10 (m) (2H, C-2 protons), 3.06 (m) (4H, C-1 and C-3 protons), 7.55 (bs) (5H, phenyl protons), 7.76 (bs) (1H, =CH—), 8.39 (d) (1H, C-6 proton), 9.06 (dd) (1H, C-7 proton), 10.13 (d) (1H, C-9 proton).

EXAMPLE 16

1,2,3,4-tetrahydro-11-oxo-11H-pyrido[2,1-b]quinazoline-8-carboxylic acid, methyl ester (2.5 g) was reacted with 2-methoxy-benzaldehyde (2.6 g) in tert.butanol (75 ml) in the presence of potassium tert.butylate (4.3 g) under stirring at reflux temperature for 8 hours. After cooling the solution was concentrated in vacuo to a small volume and the precipitate was filtered and washed with little methanol and then dissolved in water containing NaHCO₃: the solution was acidified with 23% HCl to pH=4 and the precipitate was filtered and washed with water until neutral. Crystallization from acetone gave 1.1 g of 4-(2-methoxy-benzylidene)-1,2,3,4-tetrahydro-11-oxo-11H-pyrido[2,1-b]quinazoline-8-carboxylic acid, m.p. 300° C. (dec.), N.M.R. (CDCl₃-CF₃COOD) δp.p.m.: 1.93 (m) (2H,C-2 protons), 2.84 (m) (4H, C-1 and C-3 protons), 3.81 (s) (3H, —OCH₃), 6.80–7.50 (m) (4H, phenyl protons), 7.70 (bs) (1H, =CH—), 8.17 (d) (1H, C-6 proton), 8.69 (dd) (1H, C-7 proton), 9.73 (d) (1H,C-9 proton).

EXAMPLE 17

By proceeding according to Example 15 and 16 the following compounds were prepared:
4-(3-methyl-benzylidene)-1,2,3,4-tetrahydro-11-oxo-11H-pyrido[2,1-b]quinazoline-8-carboxylic acid, m.p. 281°–284° C.;
4-(4-methyl-benzylidene)-1,2,3,4-tetrahydro-11-oxo-11H-pyrido[2,1-b]quinazoline-8-carboxylic acid;
4-(2-methyl-benzylidene)-1,2,3,4-tetrahydro-11-oxo-11H-pyrido[2,1-b]quinazoline-8-carboxylic acid, m.p. 295°–300° C. dec;
4-(3-methoxy-benzylidene)-1,2,3,4-tetrahydro-11-oxo-11H-pyrido[2,1-b]quinazoline-8-carboxylic acid, m.p. 239°–243° C.;
4-(4-methoxy-benzylidene)-1,2,3,4-tetrahydro-11-oxo-11H-pyrido[2,1-b]quinazoline-8-carboxylic acid, m.p. 263°–267° C.;
4-(2-ethoxy-benzylidene)-1,2,3,4-tetrahydro-11-oxo-11H-pyrido[2,1-b]quinazoline-8-carboxylic acid, m.p. 269°–271° C.;
4-(3-ethoxy-benzylidene)-1,2,3,4-tetrahydro-11-oxo-11H-pyrido[2,1-b]quinazoline-8-carboxylic acid, m.p. 257°–260° C.;
4-(4-ethoxy-benzylidene)-1,2,3,4-tetrahydro-11-oxo-11H-pyrido[2,1-b]quinazoline-8-carboxylic acid, m.p. 285°–288° C.;
4-(2,5-dimethyl-benzylidene)-1,2,3,4-tetrahydro-11-oxo-11H-pyrido[2,1-b]quinazoline-8-carboxylic acid, m.p. 225°–227° C.;
4-(2,3-dimethoxy-benzylidene)-1,2,3,4-tetrahydro-11-oxo-11H-pyrido[2,1-b]quinazoline-8-carboxylic acid, m.p. 280°–5° C. dec;
4-(2,5-dimethoxy-benzylidene)-1,2,3,4-tetrahydro-11-oxo-11H-pyrido[2,1-b]quinazoline-8-carboxylic acid, m.p.265°–8° C.;
4-(3,4-dimethoxy-benzylidene)-1,2,3,4-tetrahydro-11-oxo-11H-pyrido[2,1-b]quinazoline-8-carboxylic acid, m.p. 266°–8° C.;
4-(3,4-methylenedioxy-benzylidene)-1,2,3,4-tetrahydro-11-oxo-11H-pyrido[2,1-b]quinazoline-8-carboxylic acid, m.p. 294°–297° C.;
4-(4-fluoro-benzylidene)-1,2,3,4-tetrahydro-11-oxo-11H-pyrido[2,1-b]quinazoline-8-carboxylic acid, m.p. 270°–274° C.;

4-(2-chloro-benzylidene)-1,2,3,4-tetrahydro-11-oxo-11H-pyrido[2,1-b]quinazoline-8-carboxylic acid, m.p. 245°–247° C.;

4-(3-chloro-benzylidene)-1,2,3,4-tetrahydro-11-oxo-11H-pyrido[2,1-b]quinazoline-8-carboxylic acid, m.p. 285°–293° C.;

4-(4-chloro-benzylidene)-1,2,3,4-tetrahydro-11-oxo-11H-pyrido[2,1-b]quinazoline-8-carboxylic acid, m.p. 320°–327° C.;

4-(2-methoxy-3-ethoxy-benzylidene)-1,2,3,4-tetrahydro-11-oxo-11H-pyrido[2,1-b]quinazoline-8-carboxylic acid, m.p. 210°–212° C.;

4-(2-thenylidene)-1,2,3,4-tetrahydro-11-oxo-11H-pyrido[2,1-b]quinazoline-8-carboxylic acid, m.p. 296°–299° C.;

4-[(2-pyridyl)-methylene]-1,2,3,4-tetrahydro-11-oxo-11H-pyrido[2,1-b]quinazoline-8-carboxylic acid;

4-[(3-pyridyl)-methylene]-1,2,3,4-tetrahydro-11-oxo-11H-pyrido[2,1-b]quinazoline-8-carboxylic acid;

4-[(4-pyridyl)-methylene]-1,2,3,4-tetrahydro-11-oxo-11H-pyrido[2,1-b]quinazoline-8-carboxylic acid;

4-(2-furfurylidene)-1,2,3,4-tetrahydro-11-oxo-11H-pyrido[2,1-b]quinazoline-8-carboxylic acid;

4-(2,4-dimethoxy-benzylidene)-1,2,3,4-tetrahydro-11-oxo-11H-pyrido[2,1-b]quinazoline-8-carboxylic acid;

4-(3,5-dimethoxy-benzylidene)-1,2,3,4-tetrahydro-11-oxo-11H-pyrido[2,1-b]quinazoline-8-carboxylic acid;

4-(2-ethoxy-3-methoxy-benzylidene)-1,2,3,4-tetrahydro-11-oxo-11H-pyrido[2,1-b]quinazoline-8-carboxylic acid;

4-(2,3,4-trimethoxy-benzylidene)-1,2,3,4-tetrahydro-11-oxo-11H-pyrido[2,1-b]quinazoline-8-carboxylic acid, m.p. 225°–230° C.(dec.);

4-(3,4,5-trimethoxy-benzylidene)-1,2,3,4-tetrahydro-11-oxo-11H-pyrido[2,1-b]quinazoline-8-carboxylic acid, m.p. 259°–261° C.;

4-(2,4,5-trimethoxy-benzylidene)-1,2,3,4-tetrahydro-11-oxo-11H-pyrido[2,1-b]quinazoline-8-carboxylic acid;

4-(3-hydroxy-benzylidene)-1,2,3,4-tetrahydro-11-oxo-11H-pyrido[2,1-b]quinazoline-8-carboxylic acid;

4-(4-hydroxy-benzylidene)-1,2,3,4-tetrahydro-11-oxo-11H-pyrido[2,1-b]quinazoline-8-carboxylic acid;

4-(2-nitro-benzylidene)-1,2,3,4-tetrahydro-11-oxo-11H-pyrido[2,1-b]quinazoline-8-carboxylic acid;

4-(3-nitro-benzylidene)-1,2,3,4-tetrahydro-11-oxo-11H-pyrido[2,1-b]quinazoline-8-carboxylic acid;

4-(4-nitro-benzylidene)-1,2,3,4-tetrahydro-11-oxo-11H-pyrido[2,1-b]quinazoline-8-carboxylic acid;

4-(4-dimethylamino-benzylidene)-1,2,3,4-tetrahydro-11-oxo-11H-pyrido[2,1-b]quinazoline-8-carboxylic acid, m.p. 262°–267° C.;

4-(2,6-dichloro-benzylidene)-1,2,3,4-tetrahydro-11-oxo-11H-pyrido[2,1-b]quinazoline-8-carboxylic acid, m.p. 320°–330° C., dec.;

4-(3,4-dichloro-benzylidene)-1,2,3,4-tetrahydro-11-oxo-11H-pyrido[2,1-b]quinazoline-8-carboxylic acid, m.p. 285°–290° C.(dec.);

4-(2,4-dichloro-benzylidene)-1,2,3,4-tetrahydro-11-oxo-11H-pyrido[2,1-b]quinazoline-8-carboxylic acid, m.p. 260°–265° C.(dec.);

4-(2,4-dimethyl-benzylidene)-1,2,3,4-tetrahydro-11-oxo-11H-pyrido[2,1-b]quinazoline-8-carboxylic acid;

4-(2-isopropoxy-benzylidene)-1,2,3,4-tetrahydro-11-oxo-11H-pyrido[2,1-b]quinazoline-8-carboxylic acid;

4-(3-isopropoxy-benzylidene)-1,2,3,4-tetrahydro-11-oxo-11H-pyrido[2,1-b]quinazoline-8-carboxylic acid;

4-(4-isopropoxy-benzylidene)-1,2,3,4-tetrahydro-11-oxo-11H-pyrido[2,1-b]quinazoline-8-carboxylic acid;

4-(2-propoxy-benzylidene)-1,2,3,4-tetrahydro-11-oxo-11H-pyrido[2,1-b]quinazoline-8-carboxylic acid;

4-(3-propoxy-benzylidene)-1,2,3,4-tetrahydro-11-oxo-11H-pyrido[2,1-b]quinazoline-8-carboxylic acid; and 4-(4-propoxy-benzylidene)-1,2,3,4-tetrahydro-11-oxo-11H-pyrido[2,1-b]quinazoline-8-carboxylic acid.

EXAMPLE 18

By proceeding according to Example 15, starting from 1,2,3,10-tetrahydro-10-oxo-cyclopenta[d]pyrido[1,2-a]pyrimidine-7-carboxylic acid, methyl ester and using suitable heterocyclic aldehydes, the following compounds were prepared:

3-(2-thenylidene)-1,2,3,10-tetrahydro-10-oxo-cyclopenta[d]pyrido[1,2,-a]pyrimidine-7-carboxylic acid, m.p. 325°–327° C.;

3-[(2-pyridyl)-methylene]-1,2,3,10-tetrahydro-10-oxo-cyclopenta[d]pyrido[1,2-a]pyrimidine-7-carboxylic acid;

3-[(3-pyridyl)-methylene]-1,2,3,10-tetrahydro-10-oxo-cyclopenta[d]pyrido[1,2-a]pyrimidine-7-carboxylic acid;

3-[(4-pyridyl)-methylene]-1,2,3,10-tetrahydro-10-oxo-cyclopenta[d]pyrido[1,2-a]pyrimidine-7-carboxylic acid; and 3-(2-furfurylidene)-1,2,3,10-tetrahydro-10-oxo-cyclopenta[d]pyrido[1,2-a]pyrimidine-7-carboxylic acid.

EXAMPLE 19

By proceeding according to Examples 15 and 16, starting from suitable substituted 1,2,3,4-tetrahydro-11H-pyrido[2,1-b]quinazoline-11-ones, the following compounds were prepared:

4-benzylidene-1,2,3,4-tetrahydro-11H-pyrido[2,1-b]quinazoline-11-one;

4-(2-methyl-benzylidene)-1,2,3,4-tetrahydro-11H-pyrido[2,1-b]quinazoline-11-one, m.p. 130°–131° C.;

4-(2-chloro-benzylidene)-1,2,3,4-tetrahydro-11H-pyrido[2,1-b]quinazoline-11-one, m.p. 145°–146° C.;

4-benzylidene-8-chloro-1,2,3,4-tetrahydro-11H-pyrido[2,1-b]quinazoline-11-one;

8-chloro-4-(2-methyl-benzylidene)-1,2,3,4-tetrahydro-11H-pyrido[2,1-b]quinazoline-11-one, m.p. 189°–190° C.;

8-chloro-4-[(3-pyridyl)-methylene]-1,2,3,4-tetrahydro-11H-pyrido[2,1-b]quinazoline-11-one, m.p. 201°–202° C.;

4-benzylidene-8-methyl-1,2,3,4-tetrahydro-11H-pyrido[2,1-b]quinazoline-11-one;

4-benzylidene-7-methyl-1,2,3,4-tetrahydro-11H-pyrido[2,1-b]quinazoline-11-one;

4-(2-methoxy-benzylidene)-8-methyl-1,2,3,4-tetrahydro-11H-pyrido[2,1-b]quinazoline-11-one;

4-(3-methoxy-benzylidene)-8-methyl-1,2,3,4-tetrahydro-11H-pyrido[2,1-b]quinazoline-11-one;

4-(2,6-dichloro-benzylidene)-8-methyl-1,2,3,4-tetrahydro-11H-pyrido[2,1-b]quinazoline-11-one;

4-(4-methoxy-benzylidene)-8-methyl-1,2,3,4-tetrahydro-11H-pyrido[2,1-b]quinazoline-11-one;

4-(2,3-dimethoxy-benzylidene)-8-methyl-1,2,3,4-tetrahydro-11H-pyrido[2,1-b]quinazoline-11-one;

4-(2,5-dimethoxy-benzylidene)-8-methyl-1,2,3,4-tetrahydro-11H-pyrido[2,1-b]quinazoline-11-one;

4-(2-methoxy-3-ethoxy-benzylidene)-8-methyl-1,2,3,4-tetrahydro-11H-pyrido[2,1-b]quinazoline-11-one;

4-(2,5-dimethyl-benzylidene)-8-methyl-1,2,3,4-tetrahydro-11H-pyrido[2,1-b]quinazoline-11-one;

8-methyl-4-(2-methyl-benzylidene)-1,2,3,4-tetrahydro-11H-pyrido[2,1-b]quinazoline-11-one;
8-methyl-4-(3-methyl-benzylidene)-1,2,3,4-tetrahydro-11H-pyrido[2,1-b]quinazoline-11-one;
8-methyl-4-(4-methyl-benzylidene)-1,2,3,4-tetrahydro-11H-pyrido[2,1-b]quinazoline-11-one;
8-methyl-4-(2-thenylidene)-1,2,3,4-tetrahydro-11H-pyrido[2,1-b]quinazoline-11-one;
8-methyl-4-[(2-pyridyl)-methylene]-1,2,3,4-tetrahydro-11H-pyrido[2,1-b]quinazoline-11-one;
8-methyl-4-[(3-pyridyl)-methylene]-1,2,3,4-tetrahydro-11H-pyrido[2,1-b]quinazoline-11-one; and
8-methyl-4-[(4-pyridyl)-methylene]-1,2,3,4-tetrahydro-11H-pyrido-[2,1-b]quinazoline-11-one.

EXAMPLE 20

4-benzylidene-1,2,3,4-tetrahydro-11-oxo-11H-pyrido[2,1-b]quinazoline-8-carboxylic acid (1 g) was reacted with methyl iodide (1.25 g) and anhydrous $K_2CO_3$ (1.15 g) in dimethylformamide (40 ml) under stirring at room temperature for 24 hours. Dilution with ice water gave a precipitate which was filtered and washed with water until neutral: 0.9 g of 4-benzylidene-1,2,3,4-tetrahydro-11-oxo-11H-pyrido[2,1-b]quinazoline-8-carboxylic acid, methyl ester were obtained, m.p. 166°–168° C.

By proceeding analogously with the following compounds were prepared:
4-benzylidene-1,2,3,4-tetrahydro-11-oxo-11H-pyrido[2,1-b]quinazoline-8-carboxylic acid, ethyl ester;
4-(2-methyl-benzylidene)-1,2,3,4-tetrahydro-11-oxo-11H-pyrido[2,1-b]quinazoline-8-carboxylic acid, methyl ester;
4-(3-methyl-benzylidene)-1,2,3,4-tetrahydro-11-oxo-11H-pyrido[2,1-b]quinazoline-8-carboxylic acid, methyl ester;
4-(4-methyl-benzylidene)-1,2,3,4-tetrahydro-11-oxo-11H-pyrido[2,1-b]quinazoline-8-carboxylic acid, methyl ester;
4-(2-methoxy-benzylidene)-1,2,3,4-tetrahydro-11-oxo-11H-pyrido[2,1-b]quinazoline-8-carboxylic acid, methyl ester;
4-(3-methoxy-benzylidene)-1,2,3,4-tetrahydro-11-oxo-11H-pyrido[2,1-b]quinazoline-8-carboxylic acid, methyl ester; and
4-(4-methoxy-benzylidene)-1,2,3,4-tetrahydro-11-oxo-11H-pyrido[2,1-b]quinazoline-8-carboxylic acid, methyl ester.

EXAMPLE 21

Trimethyl-sulphoxonium iodide (1.8 g) was reacted with 50% sodium hydride (0.39 g) in dimethylformamide (20 ml) under stirring at room temperature for 60 minutes, then a solution of 4-benzylidene-1,2,3,4-tetrahydro-11-oxo-11H-pyrido[2,1-b]quinazoline-8-carboxylic acid methyl ester (2.7 g) in dimethylformamide (30 ml) was added.

The mixture was allowed to react at room temperature for 1 hour then it was diluted with ice water and neutralized with acetic acid. The precipitate was filtered and washed with water to give 2.25 g of 4-benzylidene-8,9-methylene-1,2,3,4-tetrahydro-11-oxo-11H-pyrido[2,1-b]quinazoline-8-carboxylic acid methyl ester, m.p. 228°–230° C., which was treated with 0.5% KOH in 95% ethanol solution (80 ml) at reflux temperature for 15 minutes. After cooling the reaction mixture was acidified with acetic acid and diluted with water: the precipitate was filtered, washed with wafter until neutral and crystallized from $CH_2Cl_2$/methanol to give 1.3 g of 4-benzylidene-8,9-methylene-1,2,3,4-tetrahydro-11-oxo-11H-pyrido[2,1-b]quinazoline-8-carboxylic acid, m.p. 240°–243° C.

By proceeding analogously the following compounds were prepared:
4-(2-methyl-benzylidene)-8,9-methylene-1,2,3,4-tetrahydro-11-oxo-11H-pyrido[2,1-b]quinazoline-8-carboxylic acid;
4-(3-methyl-benzylidene)-8,9-methylene-1,2,3,4-tetrahydro-11-oxo-11-pyrido[2,1-b]quinazoline-8-carboxylic acid;
4-(4-methyl-benzylidene)-8,9-methylene-1,2,3,4-tetrahydro-11-oxo-11H-pyrido[2,1-b]quinazoline-8-carboxylic acid;
4-(2-methoxy-benzylidene)-8,9-methylene-1,2,3,4-tetrahydro-11-oxo-11H-pyrido[2,1-b]quinazoline-8-carboxylic acid;
4-(3-methoxy-benzylidene)-8,9-methylene-1,2,3,4-tetrahydro-11-oxo-11H-pyrido[2,1-b]quinazoline-8-carboxylic acid;
4-(4-methoxy-benzylidene)-8,9-methylene-1,2,3,4-tetrahydro-11-oxo-11H-pyrido[2,1-b]quinazoline-8-carboxylic acid;
4-(2-ethoxy-benzylidene)-8,9-methylene-1,2,3,4-tetrahydro-11-oxo-11H-pyrido[2,1-b]quinazoline-8-carboxylic acid;
4-(3-ethoxy-benzylidene)-8,9-methylene-1,2,3,4-tetrahydro-11-oxo-11H-pyrido[2,1-b]quinazoline-8-carboxylic acid;
4-(4-ethoxy-benzylidene)-8,9-methylene-1,2,3,4-tetrahydro-11-oxo-11H-pyrido[2,1-b]quinazoline-8-carboxylic acid;
4-(2,5-dimethyl-benzylidene)-8,9-methylene-1,2,3,4-tetrahydro-11-oxo-11H-pyrido[2,1-b]quinazoline-8-carboxylic acid;
4-(2,3-dimethoxy-benzylidene)-8,9-methylene-1,2,3,4-tetrahydro-11-oxo-11H-pyrido[2,1-b]quinazoline-8-carboxylic acid;
4-(2,5-dimethoxy-benzylidene)-8,9-methylene-1,2,3,4-tetrahydro-11-oxo-11H-pyrido[2,1-b]quinazoline-8-carboxylic acid;
4-(3,4-dimethoxy-benzylidene)-8,9-methylene-1,2,3,4-tetrahydro-11-oxo-11H-pyrido[2,1-b]quinazoline-8-carboxylic acid;
4-(2,3,4-trimethoxy-benzylidene)-8,9-methylene-1,2,3,4-tetrahydro-11-oxo-11H-pyrido[2,1-b]quinazoline-8-carboxylic acid;
4-(3,4,5-trimethoxy-benzylidene)-8,9-methylene-1,2,3,4-tetrahydro-11-oxo-11H-pyrido[2,1-b]quinazoline-8-carboxylic acid;
4-(3,4-methylenedioxy-benzylidene)-8,9-methylene-1,2,3,4-tetrahydro-B 11-oxo-11H-pyrido[2,1-b]quinazoline-8-carboxylic acid;
4-(4-fluoro-benzylidene)-8,9-methylene-1,2,3,4-tetrahydro-11-oxo-11H-pyrido[2,1-b]quinazoline-8-carboxylic acid;
4-(2-chloro-benzylidene)-8,9-methylene-1,2,3,4-tetrahydro-11-oxo-11H-pyrido[2,1-b]quinazoline-8-carboxylic acid;
4-(3-chloro-benzylidene)-8,9-methylene-1,2,3,4-tetrahydro-11-oxo-11H-pyrido[2,1-b]quinazoline-8-carboxylic acid;
4-(4-chloro-benzylidene)-8,9-methylene-1,2,3,4-tetrahydro-11-oxo-11H-pyrido[2,1-b]quinazoline-8-carboxylic acid;

4-(2,6-dichloro-benzylidene)-8,9-methylene-1,2,3,4-tetrahydro-11-oxo-11H-pyrido[2,1-b]quinazoline-8-carboxylic acid;

4-(3,4-dichloro-benzylidene)-8,9-methylene-1,2,3,4-tetrahydro-11-oxo-11H-pyrido[2,1-b]quinazoline-8-carboxylic acid;

4-(2-methoxy-3-ethoxy-benzylidene)-8,9-methylene-1,2,3,4-tetrahydro-11-oxo-11H-pyrido[2,1-b]quinazoline-8-carboxylic acid;

4-(2-thenylidene)-8,9-methylene-1,2,3,4-tetrahydro-11-oxo-11H-pyrido[2,1-b]quinazoline-8-carboxylic acid;

4-[(2-pyridyl)-methylene]-8,9-methylene-1,2,3,4-tetrahydro-11-oxo-11H-pyrido[2,1-b]quinazoline-8-carboxylic acid;

4-[(3-pyridyl)-methylene]-8,9-methylene-1,2,3,4-tetrahydro-11-oxo-11H-pyrido[2,1-b]quinazoline-8-carboxylic acid; and 4-(4-pyridyl)-methylene]-8,9-methylene-1,2,3,4-tetrahydro-11-oxo-11H-pyrido[2,1-b]quinazoline-8-carboxylic acid.

EXAMPLE 22

4-benzylidene-1,2,3,4-tetrahydro-11-oxo-11H-pyrido[2,1-b]quinazoline-8-carboxylic acid (0.5 g) was reacted with $SOCl_2$ (0.25 g) in dioxane (250 ml) at the reflux temperature for 2 hours. After cooling the reaction mixture was evaporated in vacuo to dryness and the residue was dissolved in dioxane (70 ml) and reacted with 2-(N,N-diethylamino)-ethanol (3.5 g) under stirring at room temperature for 20 hours.

The reaction mixture was concentrated in vacuo to a small volume and then diluted with ice water: the precipitate was extracted with chloroform and the organic solution was evaporated in vacuo to dryness.

Crystallization of the residue from $CH_2Cl_2$-isopropyl ether gave 2.9 g of 4-benzylidene-1,2,3,4-tetrahydro-11-oxo-11H-pyrido[2,1-b]quinazoline-8-carboxylic acid, 2-(N,N-diethylamino)-ethyl ester, m.p. 95°–97° C. N.M.R. ($CDCl_3$) δ p.p.m.: 1.08 (t) (6H, $—CH_2—CH_3$), 1.84 (m) (2H, C-2 protons), 2.62 (q) (4H, $—CH_2—CH_3$), 2.85 (m) (6H; C-1 and C-3 protons; $—COOCH_2CH_2—N<$), 4.41 (t) (2H, 13 $COOCH_2CH_2N<$), 7.35 (m) (5H, phenyl protons), 7.48 (d) (1H, C-6 proton), 7.98 (dd) (1H, C-7 proton), 8.12 (bs) (1H, $=CH—$), 9.50 (d) (1H, C-9 proton). By proceeding analogously, the following compounds were prepared:

4-benzylidene-1,2,3,4-tetrahydro-11-oxo-11H-pyrido[2,1-b]quinazoline-8-carboxylic acid, 2-(N,N-dimethylamino)-ethyl ester;

4-(2-thenylidene)-1,2,3,4-tetrahydro-11-oxo-11H-pyrido[2,1-b]quinazoline-8-carboxylic acid, 2-(N,N-diethylamino)-ethyl ester;

4-[(2-pyridyl)-methylene]-1,2,3,4-tetrahydro-11-oxo-11H-pyrido[2,1-b]quinazoline-8-carboxylic acid, 2-(N,N-diethylamino)-ethyl ester;

4-[(3-pyridyl)-methylene]-1,2,3,4-tetrahydro-11-oxo-11H-pyrido[2,1-b]quinazoline-8-carboxylic acid, 2-(N,N-diethylamino)-ethyl ester;

4-(2-methyl-benzylidene)-1,2,3,4-tetrahydro-11-oxo-11H-pyrido[2,1-b]quinazoline-8-carboxylic acid, 2-(N,N-diethylamino)-ethyl ester;

4-(3-methyl-benzylidene)-1,2,3,4-tetrahydro-11-oxo-11H-pyrido[2,1-b]quinazoline-8-carboxylic acid, 2-(N,N-diethylamino)-ethyl ester;

4-(4-methyl-benzylidene)-1,2,3,4-tetrahydro-11-oxo-11H-pyrido[2,1-b]quinazoline-8-carboxylic acid, 2-(N,N-diethylamino)-ethyl ester;

4-(2-methoxy-benzylidene)-1,2,3,4-tetrahydro-11-oxo-11H-pyrido[2,1-b]quinazoline-8-carboxylic acid, 2-(N,N-diethylamino)-ethyl ester;

4-(3-methoxy-benzylidene)-1,2,3,4-tetrahydro-11-oxo-11H-pyrido[2,1-b]quinazoline-8-carboxylic acid, 2-(N,N-diethylamino)-ethyl ester;

4-(4-methoxy-benzylidene)-1,2,3,4-tetrahydro-11-oxo-11H-pyrido[2,1-b]quinazoline-8-carboxylic acid, 2-(N,N-diethylamino)-ethyl ester;

4-(2-ethoxy-benzylidene)-1,2,3,4-tetrahydro-11-oxo-11H-pyrido[2,1-b]quinazoline-8-carboxylic acid, 2-(N,N-diethylamino)-ethyl ester;

4-(3-ethoxy-benzylidene)-1,2,3,4-tetrahydro-11-oxo-11H-pyrido[2,1-b]quinazoline-8-carboxylic acid, 2-(N,N-diethylamino)-ethyl ester;

4-(4-ethoxy-benzylidene)-1,2,3,4-tetrahydro-11-oxo-11H-pyrido[2,1-b]quinazoline-8-carboxylic acid, 2-(N,N-diethylamino)-ethyl ester;

4-(2,5-dimethyl-benzylidene)-1,2,3,4-tetrahydro-11-oxo-11H-pyrido[2,1-b]quinazoline-8-carboxylic acid, 2-(N,N-diethylamino)-ethyl ester;

4-(2,3-dimethoxy-benzylidene)-1,2,3,4-tetrahydro-11-oxo-11H-pyrido[2,1-b]quinazoline-8-carboxylic acid, 2-(N,N-diethylamino)-ethyl ester;

4-(2,5-dimethoxy-benzylidene)-1,2,3,4-tetrahydro-11-oxo-11H-pyrido[2,1-b]quinazoline-8-carboxylic acid, 2-(N,N-diethylamino)-ethyl ester;

4-(3,4-dimethoxy-benzylidene)-1,2,3,4-tetrahydro-11-oxo-11H-pyrido[2,1-b]quinazoline-8-carboxylic acid, 2-(N,N-diethylamino)-ethyl ester;

4-(2-methoxy-3-ethoxy-benzylidene)-1,2,3,4-tetrahydro-11-oxo-11H-pyrido[2,1-b]quinazoline-8-carboxylic acid, 2-(N,N-diethylamino)-ethyl ester;

4-(2-chloro-benzylidene)-1,2,3,4-tetrahydro-11-oxo-11H-pyrido[2,1-b]quinazoline-8-carboxylic acid, 2-(N,N-diethylamino)-ethyl ester;

4-(3-chloro-benzylidene)-1,2,3,4-tetrahydro-11-oxo-11H-pyrido[2,1-b]quinazoline-8-carboxylic acid, 2-(N,N-diethylamino)-ethyl ester;

4-(4-chloro-benzylidene)-1,2,3,4-tetrahydro-11-oxo-11H-pyrido[2,1-b]quinazoline-8-carboxylic acid, 2-(N,N-diethylamino)-ethyl ester;

4-(2,6-dichloro-benzylidene)-1,2,3,4-tetrahydro-11-oxo-11H-pyrido[2,1-b]quinazoline-8-carboxylic acid, 2-(N,N-diethylamino)-ethyl ester;

4-(3,4-dichloro-benzylidene)-1,2,3,4-tetrahydro-11-oxo-11H-pyrido[2,1-b]quinazoline-8-carboxylic acid, 2-(N,N-diethylamino)-ethyl ester; and 4-(2,4-dichloro-benzylidene)-1,2,3,4-tetrahydro-11-oxo-11H-pyrido[2,1-b]quinazoline-8-carboxylic acid, 2-(N,N-diethylamino)-ethyl ester.

EXAMPLE 23

4-(4-nitro-benzylidene)-1,2,3,4-tetrahydro-11-oxo-11H-pyrido[2,1-b]quinazoline-8-carboxylic acid, methyl ester (3.23 g), was reacted with $SnCl_2.2H_2O$ (17 g) in 37% HCl (12.5 ml) and acetic acid (40 ml) under stirring at 60° C. for 2 hours. After cooling the precipitate, 4-(4-amino-benzylidene)-1,2,3,4-tetrahydro-11-oxo-11H-pyrido[2,1-b]quinazoline-8-carboxylic acid methyl ester, was filtered and washed with water and then dissolved in dimethylformamide (60 ml) and treated with 2N NaOH (15 ml) at room temperature for 3 hours. After acidification with acetic acid and dilution with ice water the precipitate that formed was filtered and washed with water: crystallization from dimethylformamide gave 2.1 g of 4-(4-amino-benzylidene)-

1,2,3,4-tetrahydro-11-oxo-11H-pyrido[2,1-b]quinazoline-8-carboxylic acid.

By proceeding analogously the following compounds were prepared:
4-(3-amino-benzylidene)-1,2,3,4-tetrahydro-11-oxo-11H-pyrido[2,1-b]quinazoline-8-carboxylic acid;
4-(2-amino-benzylidene)-1,2,3,4-tetrahydro-11-oxo-11H-pyrido[2,1-b]quinazoline-8-carboxylic acid; and
4-(4-amino-benzylidene)-8-methyl-1,2,3,4-tetrahydro-11H-pyrido[2,1-b]quinazoline-11-one.

EXAMPLE 24

4-(4-amino-benzylidene)-1,2,3,4-tetrahydro-11-oxo-11H-pyrido[2,1-b]quinazoline-8-carboxylic acid (1 g) in dimethylformamide (40 ml) was reacted with acetic anhydride (4 ml) in the presence of pyridine (8 ml) at 60° C. for 7 hours. After cooling and dilution with ice water, the precipitate was filtered and washed with water: crystallization from dimethylformamide-ethanol gave 0.7 g of 4-(4-acetylamino-benzylidene)-1,2,3,4-tetrahydro-11-oxo-11H-pyrido[2,1-b]quinazoline-8-carboxylic acid.

By proceeding analogously the following compounds were prepared:
4-(3-acetylamino-benzylidene)-1,2,3,4-tetrahydro-11-oxo-11H-pyrido[2,1-b]quinazoline-8-carboxylic acid;
4-(2-acetylamino-benzylidene)-1,2,3,4-tetrahydro-11-oxo-11H-pyrido[2,1-b]quinazoline-8-carboxylic acid;
4-(4-acetoxy-benzylidene)-1,2,3,4-tetrahydro-11-oxo-11H-pyrido[2,1-b]quinazoline-8-carboxylic acid;
4-(3-acetoxy-benzylidene)-1,2,3,4-tetrahydro-11-oxo-11H-pyrido[2,1-b]quinazoline-8-carboxylic acid; and
4-(4-acetylamino-benzylidene)-8-methyl-1,2,3,4-tetrahydro-11H-pyrido[2,1-b]quinazoline-11-one.

EXAMPLE 25

4-benzylidene-1,2,3,4-tetrahydro-11-oxo-11H-pyrido[2,1-b]quinazoline-8-carboxylic acid was treated with the stoichiometric amount of sodium methoxide in methanol at 60° C. for 10 minutes.

After concentration in vacuo to a small volume the precipitate was filtered and washed with a little amount of cold methanol and then with hexane: 4-benzylidene-1,2,3,4-tetrahydro-11-oxo-11H-pyrido[2,1-b]quinazoline-8-carboxylic acid, sodium salt, m.p. >300° C. was obtained.

By proceeding analogously the following compounds were prepared:
4-(2-methoxy-benzylidene)-1,2,3,4-tetrahydro-11-oxo-11H-pyrido[2,1-b]quinazoline-8-carboxylic acid, sodium salt;
4-(3-methoxy-benzylidene)-1,2,3,4-tetrahydro-11-oxo-11H-pyrido[2,1-b]quinazoline-8-carboxylic acid, sodium salt;
4-(4-methoxy-benzylidene)-1,2,3,4-tetrahydro-11-oxo-11H-pyrido[2,1-b]quinazoline-8-carboxylic acid, sodium salt;
4-(2,3-dimethoxy-benzylidene)-1,2,3,4-tetrahydro-11-oxo-11H-pyrido[2,1-b]quinazoline-8-carboxylic acid, sodium salt;
4-(2-methyl-benzylidene)-1,2,3,4-tetrahydro-11-oxo-11H-pyrido[2,1-b]quinazoline-8-carboxylic acid, sodium salt; and
4-(2,6-dichloro-benzylidene)-1,2,3,4-tetrahydro-11-oxo-11H-pyrido[2,1-b]quinazoline-8-carboxylic acid, sodium salt.

EXAMPLE 26

Tablets, each weighing 200 mg and containing 100 mg of the active substance were manufactured as follows:

Composition (for 10,000 tablets)

| | |
|---|---|
| 3-benzylidene-1,2,3,10-tetrahydro-10-oxo-cyclopenta[d]pyrido[1,2-a]pyrimidine-7-carboxylic acid | 1000 g |
| lactose | 710 g |
| corn starch | 237.5 g |
| talc powder | 37.5 g |
| magnesium stearate | 15 g |

The 3-benzylidene-1,2,3,10-tetrahydro-10-oxo-cyclopenta[d]pyrido[1,2-a]pyrimidine-7-carboxylic acid, lactose and half the corn starch were mixed. The mixture was then forced through a sieve having 0.5 mm openings. Corn starch (18 g) was suspended in warm water (180 ml). The resulting paste was used to granulate the powder. The granules were dried and comminuted on a sieve having 1.4 mm openings. The remaining starch, talc and magnesium stearate were added, carefully mixed and processed into tablets using punches of 8 mm diameter.

EXAMPLE 27

Tablets, each weighing 200 mg and containing 100 mg of the active substance were manufactured as follows:

Composition (for 10,000 tablets)

| | |
|---|---|
| 4-benzylidene-1,2,3,4-tetrahydro-11-oxo-11H—pyrido[2,1-b]quinazoline-8-carboxylic acid | 1000 g |
| Lactose | 710 g |
| Corn starch | 237.5 g |
| Talc powder | 37.5 g |
| Magnesium stearate | 15 g |

The 4-benzylidene-1,2,3,4-tetrahydro-11-oxo-11H-pyrido[2,1-b]quinazoline-8-carboxylic acid, lactose and half the corn starch were mixed. The mixture was then forced through a sieve having 0.5 mm openings. Corn starch (18 g) was suspended in warm water (180 ml). The resulting paste was used to granulate the powder. The granules were dried and comminuted on a sieve having 1.4 mm opening. The remaining starch, talc and magnesium stearate were added, carefully mixed and processed into tablets using punches of 8 mm diameter.

We claim:
1. A compound of general formula (I)

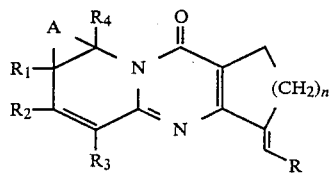

wherein
n is 1 or 2;
$R_1$ represents a hydrogen or a halogen atom, a $C_1$–$C_4$ alkyl group, a —CN group, a —CONH$_2$ group or a —COOR$_8$ group, wherein $R_8$ represents hydrogen or a $C_1$–$C_6$ alkyl group, unsubstituted or substituted by di($C_1$–$C_4$)-alkyl-amino;

each of $R_2$, $R_3$ and $R_4$ independently represents a hydrogen or a halogen atom, a $C_1$–$C_4$ alkyl group, a $C_1$–$C_4$ alkoxy group or a $C_3$–$C_4$ alkenyloxy group;

A completes a bond, thereby providing a double bond or, when $R_1$ is —$COOR_8$ wherein $R_8$ is as defined above, A may represent also a —$CH_2$— group, thereby providing a cyclopropane ring fused to the pyrido ring;

R is (a) furyl, thienyl or pyridyl; or (b) a group of formula

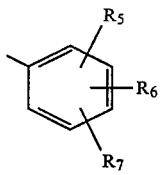

wherein each of $R_5$, $R_6$ and $R_7$ represents, independently, a hydrogen or a halogen atom, hydroxy, formyloxy, $C_2$–$C_8$ alkanoyloxy, $C_1$–$C_4$ alkyl, $C_1$–$C_4$ alkoxy, nitro or a

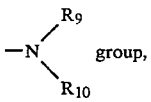

wherein each of $R_9$ and $R_{10}$ independently represents hydrogen, $C_1$–$C_4$ alkyl, formyl or $C_2$–$C_8$ alkanoyl, or adjacent groups represented by two of $R_5$, $R_6$ and $R_7$, taken together, form a $C_1$–$C_3$ alkylenedioxy group; or the pharmaceutically acceptable salts thereof.

2. A compound of formula (I), according to claim (1), wherein: $R_1$ represents hydrogen, chlorine, carboxy, methyl, or ($C_1$–$C_4$)alkoxy-carbonyl unsubstituted or substituted by a 2-N,N-di($C_1$–$C_2$)alkyl-amino group; $R_2$ is hydrogen; $R_3$ is hydrogen, chlorine, methyl or methoxy; $R_4$ is hydrogen; A completes a bond, thereby providing a double bond, or when $R_1$ is a free carboxy group, A may represent also a —$CH_2$— group, thereby providing a cyclopropane ring fused to the pyrido ring; n is 1 or 2; R is (a) furyl, thienyl or pyridyl; or (b) a group of formula

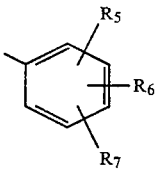

wherein, each of $R_5$, $R_6$ and $R_7$ represents independently hydrogen, chlorine, fluorine, $C_1$–$C_2$ alkyl, $C_1$–$C_3$ alkoxy, amino, dimethylamino, hydroxy or adjacent groups represented by two of $R_5$, $R_6$ and $R_7$, taken together, form a methylenedioxy group; or the pharmaceutically acceptable salts thereof.

3. 4-benzylidene-1,2,3,4-tetrahydro-11-oxo-11H-pyrido[2,1-b]quinazoline-8-carboxylic acid or its pharmaceutically acceptable salts.

4. A compound selected from the group consisting of:

3-benzylidene-1,2,3,10-tetrahydro-10-oxo-cyclopenta[d]pyrido[1,2-a]pyrimidine-7-carboxylic acid;

3-(2-methyl-benzylidene)-1,2,3,10-tetrahydro-10-oxo-cyclopenta[d]pyrido[1,2-a]pyrimidine-7-carboxylic acid;

3-(2,5-dimethoxy-benzylidene)-1,2,3,10-tetrahydro-10-oxo-cyclopenta[d]pyrido[1,2-a]pyrimidine-7-carboxylic acid;

3-(2,3-dimethoxy-benzylidene)-1,2,3,10-tetrahydro-10-oxo-cyclopenta[d]pyrido[1,2-a]pyrimidine-7-carboxylic acid;

3-(2-methoxy-3-ethoxy-benzylidene)-1,2,3,10-tetrahydro-10-oxo-cyclopenta[d]pyrido[1,2-a]pyrimidine-7-carboxylic acid.

3-(3-methyl-benzylidene)-1,2,3,10-tetrahydro-10-oxo-cyclopenta[d]pyrido[1,2,-a]pyrimidine-7-carboxylic acid;

3-(4-methyl-benzylidene)-1,2,3,10-tetrahydro-10-oxo-cyclopenta[d]pyrido[1,2-a]pyrimidine-7-carboxylic acid;

3-(2-ethoxy-benzylidene)-1,2,3,10-tetrahydro-10-oxo-cyclopenta[d]pyrido[1,2-a]pyrimidine-7-carboxylic acid;

3-(3-ethoxy-benzylidene)-1,2,3,10-tetrahydro-10-oxo-cyclopenta[d]pyrido[1,2-a]pyrimidine-7-carboxylic acid;

3-(4-methoxy-benzylidene)-1,2,3,10-tetrahydro-10-oxo-cyclopenta[d]pyrido[1,2-a]pyrimidine-7-carboxylic acid;

3-(4-ethoxy-benzylidene)-1,2,3,10-tetrahydro-10-oxo-cyclopenta[d]pyrido[1,2-a]pyrimidine-7-carboxylic acid;

3-(2-methoxy-benzylidene)-1,2,3,10-tetrahydro-10-oxo-cyclopenta-[d]pyrido[1,2-a]pyrimidine-7-carboxylic acid;

3-(3-methoxy-benzylidene)-1,2,3,10-tetrahydro-10-oxo-cyclopenta[d]pyrido[1,2-a]pyridimidine-7-carboxylic acid;

3-benzylidene-7,8-methylene-1,2,3,10-tetrahydro-10-oxo-cyclopenta[d]pyrido[1,2-a]pyrimidine-7-carboxylic acid;

3-(2-methyl-benzylidene)-7,8-methylene-1,2,3,10-tetrahydro-10-oxo-cyclopenta[d]pyrido[1,2-a]pyrimidine-7-carboxylic acid;

4-(2-methyl-benzylidene)-1,2,3,4-tetrahydro-11-oxo-11H-pyrido[2,1-b]quinazoline-8-carboxylic acid;

4-(3-methyl-benzylidene)-1,2,3,4-tetrahydro-11-oxo-11H-pyrido[2,1-b]quinazoline-8-carboxylic acid;

4-(4-methyl-benzylidene)-1,2,3,4-tetrahydro-11-oxo-11H-pyrido[2,1-b]quinazoline-8-carboxylic acid;

4-(2-methoxy-benzylidene)-1,2,3,4-tetrahydro-11-oxo-11H-pyrido[2,1-b]quinazoline-8-carboxylic acid;

4-(3-methoxy-benzylidene)-1,2,3,4-tetrahydro-11-oxo-11H-pyrido[2,1-b]quinazoline-8-carboxylic acid;

4-(4-methoxy-benzylidene)-1,2,3,4-tetrahydro-11-oxo-11H-pyrido[2,1b]quinazoline-8-carboxylic acid;

4-(2-ethoxy-benzylidene)-1,2,3,4-tetrahydro-11-oxo-11H-pyrido[2,1-b]quinazoline-8-carboxylic acid;

4-(3-ethoxy-benzylidene)-1,2,3,4-tetrahydro-11-oxo-11H-pyrido[2,1-b]quinazoline-8-carboxylic acid;

4-(4-ethoxy-benzylidene)-1,2,3,4-tetrahydro-11-oxo-11H-pyrido[2,1-b]quinazoline-8-carboxylic acid;

4-(2,5-dimethyl-benzylidene)-1,2,3,4-tetrahydro-11-oxo-11H-pyrido[2,1-b]quinazoline-8-carboxylic acid;

4-(2,3-dimethoxy-benzylidene)-1,2,3,4-tetrahydro-11-oxo-11H-pyrido[2,1-b]quinazoline-8-carboxylic acid;

4-(2,5-dimethoxy-benzylidene)-1,2,3,4-tetrahydro-11-oxo-11H-pyrido[2,1-b]quinazoline-8-carboxylic acid;

4-(2,6-dichloro-benzylidene)-1,2,3,4-tetrahydro-11-oxo-11H-pyrido[2,1-b]quinazoline-8-carboxylic acid;

4-(3,4-dichloro-benzylidene)-1,2,3,4-tetrahydro-11-oxo-11H-pyrido[2,1-b]quinazoline-8-carboxylic acid;

4-(3,4-dimethoxy-benzylidene)-1,2,3,4-tetrahydro-11-oxo-11H-pyrido[2,1-b]quinazoline-8-carboxylic acid;

4-(3,4-methylenedioxy-benzylidene)-1,2,3,4-tetrahydro-11-oxo-11H-pyrido[2,1-b]quinazoline-8-carboxylic acid;

4-(4-fluoro-benzylidene)-1,2,3,4-tetrahydro-11-oxo-11H-pyrido[2,1-b]quinazoline-8-carboxylic acid;

4-(2-chloro-benzylidene)-1,2,3,4-tetrahydro-11-oxo-11H-pyrido[2,1-b]quinazoline-8-carboxylic acid;

4-(3-chloro-benzylidene)-1,2,3,4-tetrahydro-11-oxo-11H-pyrido[2,1-b]quinazoline-8-carboxylic acid;

4-(4-chloro-benzylidene)-1,2,3,4-tetrahydro-11-oxo-11H-pyrido[2,1-b]quinazoline-8-carboxylic acid;

4-(2-methoxy-3-ethoxy-benzylidene)-1,2,3,4-tetrahydro-11-oxo-11H-pyrido[2,1-b]quinazoline-8-carboxylic acid;

4-(2-thenylidene-1,2,3,4-tetrahydro-11-oxo-11H-pyrido[2,1-b]quinazoline-8-carboxylic acid;

4-[(2-pyridyl)-methylene]-1,2,3,4-tetrahydro-11-oxo-11H-pyrido[2,1-b]quinazoline-8-carboxylic acid;

4-[(3-pyridyl)-methylene]-1,2,3,4-tetrahydro-11-oxo-11H-pyrido[2,1-b]quinazoline-8-carboxylic acid;

4-benzylidene-8,9-methylene-1,2,3,4-tetrahydro-11-oxo-11H-pyrido[2,1-b]quinazoline-8-carboxylic acid;

4-benzylidene-1,2,3,4-tetrahydro-11-oxo-11H-pyrido[2,1-b]quinazoline-8-carboxylic acid, 2-(N,N-diethylamino)-ethyl ester;

4-benzylidene-8-methyl-1,2,3,4-tetrahydro-11H-pyrido[2,1-b]quinazoline-11-one;

3-benzylidene-7-methyl-1,2,3,10-tetrahydro-cyclopenta[d]pyrido[1,2-a]pyrimidine-10-one, and the pharmaceutically acceptable salts thereof.

5. A pharmaceutical composition for the treatment of allergic conditions comprising a suitable diluent and an antiallergic effective amount of the compound according to claim 1.

6. A pharmaceutical composition for the treatment of peptic ulcers comprising a suitable diluent and an anti-ulcerogenic effective amount of the compound according to claim 1.

7. A pharmaceutical composition for the treatment of excessive gastric acid secretion comprising a suitable diluent and a gastric acid secretion inhibitory effective amount of the compound according to claim 1.

8. A method of treatment of allergic conditions in a patient in need of such treatment, said method comprising administering an anti-allergic effective amount of the compound according to claim 1.

9. A method for the treatment of peptic ulcers in a patient comprising administering an anti-ulcerogenic effective amount of the compound according to claim 1.

10. A method for inhibiting gastric acid secretion in a patient comprising administering to the patient a gastric acid secretion inhibitory effective amount of the compound according to claim 1.

* * * * *